(12) United States Patent
Preissman

(10) Patent No.: US 7,572,263 B2
(45) Date of Patent: Aug. 11, 2009

(54) HIGH PRESSURE APPLICATOR

(75) Inventor: Howard E. Preissman, Stuart, FL (US)

(73) Assignee: ArthroCare Corporation, Austin, TX (US)

( * ) Notice: Subject to any disclaimer, the term of this patent is extended or adjusted under 35 U.S.C. 154(b) by 0 days.

(21) Appl. No.: 10/301,454

(22) Filed: Nov. 20, 2002

(65) Prior Publication Data

US 2003/0078589 A1 Apr. 24, 2003

Related U.S. Application Data

(60) Continuation of application No. 10/039,892, filed on Oct. 26, 2001, now abandoned, which is a division of application No. 09/409,934, filed on Sep. 30, 1999, now Pat. No. 6,383,190, which is a continuation-in-part of application No. 09/053,108, filed on Apr. 1, 1998, now abandoned.

(51) Int. Cl.
*A61B 17/58* (2006.01)

(52) U.S. Cl. ............ 606/94; 606/92; 604/224

(58) Field of Classification Search ......... 606/92–94; 604/211, 224, 235; 222/390
See application file for complete search history.

(56) References Cited

U.S. PATENT DOCUMENTS

| 29,083 | A | | 7/1860 | Irving |
| 115,794 | A | | 6/1871 | Walsh |
| 951,160 | A | * | 3/1910 | Wainwright ............ 604/224 |
| 1,128,092 | A | | 2/1915 | Barrett |
| 1,142,210 | A | | 6/1915 | Wagner |
| 1,328,567 | A | * | 1/1920 | Jones ............ 222/390 |
| 1,709,691 | A | * | 4/1929 | Steuer ............ 604/233 |
| 2,002,610 | A | | 5/1935 | Nall ............ 221/23 |
| 2,102,591 | A | * | 12/1937 | Hagemeier ............ 604/223 |
| 2,176,042 | A | | 10/1939 | Pittenger ............ 128/272 |

(Continued)

FOREIGN PATENT DOCUMENTS

DE 34 43 167 A1 6/1986

(Continued)

OTHER PUBLICATIONS

Convery et al. (1975) "The relative safety of polymethylmethacrylate," J. of Bone and Joint Surg, 57-A(1):57:64.

(Continued)

*Primary Examiner*—Eduardo C Robert
*Assistant Examiner*—Mary Hoffman
(74) *Attorney, Agent, or Firm*—Matthew Scheele; Brian E. Szymczak

(57) ABSTRACT

A pressure applicator for applying pressure to a flowable implant material, e.g., PMMA. A pressure applicator or driver includes a pair of columns which are engageable with one another, preferably by threads to generate a driving pressure. A handle is provided for the operator to grasp and steady the device as he turns the handle to apply pressure to the implantable material within the applicator. A luer-lock or other connecting device is provided for attaching the applicator to a cannula (or a connecting conduit that in turns connects with a cannula) that will deliver the implant material to the desired site. Pressures of about 1000-3000 psi may be generated by this device.

18 Claims, 19 Drawing Sheets

U.S. PATENT DOCUMENTS

| | | | |
|---|---|---|---|
| 2,420,102 A | 5/1947 | Shuford | 128/249 |
| 2,426,535 A | 8/1947 | Turkel | 128/2 |
| 2,573,547 A | 10/1951 | Crowell | 32/60 |
| 2,676,475 A | 4/1954 | Nissen | 67/7.1 |
| 2,919,692 A | 1/1960 | Ackermann | 128/2 |
| 2,973,758 A | 3/1961 | Murrish | 128/272 |
| 3,384,274 A * | 5/1968 | Lundvall | 222/390 |
| 3,581,399 A | 6/1971 | Dragan | 32/60 |
| 3,701,771 A | 10/1972 | Almen et al. | |
| 3,750,667 A | 8/1973 | Pshenichney et al. | |
| 3,809,297 A * | 5/1974 | Poulten | 73/864.18 |
| 3,835,860 A | 9/1974 | Garretson | |
| 3,882,858 A | 5/1975 | Klemm | |
| 3,900,954 A | 8/1975 | Dragan | 32/60 |
| 3,919,773 A | 11/1975 | Freeman | |
| 3,929,708 A | 12/1975 | Brady et al. | 524/267 |
| 3,993,065 A | 11/1976 | Szabo et al. | 604/154 |
| 4,011,685 A | 3/1977 | Boyd et al. | 47/57.5 |
| 4,011,869 A | 3/1977 | Seiler, Jr. | 604/22 |
| 4,032,118 A | 6/1977 | Phillips | 366/251 |
| 4,079,518 A | 3/1978 | Marshall | 433/89 |
| 4,091,812 A | 5/1978 | Helixon et al. | 604/208 |
| 4,099,518 A | 7/1978 | Baylis et al. | 600/567 |
| 4,155,969 A | 5/1979 | Hendry | 264/45.1 |
| 4,184,490 A * | 1/1980 | Jacklich | 604/224 |
| 4,189,065 A | 2/1980 | Herold | |
| 4,232,670 A | 11/1980 | Richter et al. | 604/218 |
| 4,274,163 A | 6/1981 | Malcom et al. | |
| 4,288,355 A | 9/1981 | Anderson et al. | |
| 4,312,343 A | 1/1982 | LeVeen et al. | |
| 4,338,925 A * | 7/1982 | Miller | 606/94 |
| 4,341,691 A | 7/1982 | Anuta | |
| 4,346,708 A * | 8/1982 | LeVeen et al. | 604/224 |
| 4,364,921 A | 12/1982 | Speck et al. | |
| 4,373,217 A | 2/1983 | Draenert | |
| 4,374,093 A | 2/1983 | Rollmann et al. | 422/202 |
| 4,404,327 A | 9/1983 | Crugnola et al. | |
| 4,448,188 A | 5/1984 | Loeb | 600/108 |
| 4,469,109 A | 9/1984 | Mehl | |
| 4,551,135 A | 11/1985 | Gorman et al. | 604/82 |
| 4,554,686 A | 11/1985 | Baker | |
| 4,568,335 A * | 2/1986 | Updike et al. | 604/211 |
| 4,576,152 A * | 3/1986 | Muller et al. | 606/93 |
| 4,585,035 A | 4/1986 | Piccoli | 138/127 |
| 4,595,006 A | 6/1986 | Burke et al. | 606/94 |
| 4,610,692 A | 9/1986 | Eitenmuller et al. | |
| 4,614,437 A | 9/1986 | Buehler | 366/130 |
| 4,637,931 A | 1/1987 | Schmitz | |
| 4,653,487 A | 3/1987 | Maale | 606/62 |
| 4,653,489 A | 3/1987 | Tronzo | |
| 4,670,008 A | 6/1987 | VonAlbertini | |
| 4,671,263 A | 6/1987 | Draenert | |
| 4,699,178 A | 10/1987 | Washkewicz et al. | 138/125 |
| 4,710,179 A * | 12/1987 | Haber et al. | 604/211 |
| 4,728,570 A | 3/1988 | Ashman et al. | |
| 4,769,011 A | 9/1988 | Swaniger | 604/218 |
| 4,776,704 A | 10/1988 | Kopunek et al. | 366/184 |
| 4,791,150 A | 12/1988 | Braden et al. | |
| 4,793,363 A | 12/1988 | Ausherman et al. | |
| 4,795,444 A | 1/1989 | Hasegawa et al. | |
| 4,798,596 A | 1/1989 | Muhlbauer | |
| 4,801,263 A | 1/1989 | Clark | 433/90 |
| 4,808,184 A | 2/1989 | Tepic | 604/518 |
| 4,813,871 A | 3/1989 | Friedman | 433/90 |
| 4,815,454 A | 3/1989 | Dozier, Jr. | |
| 4,837,279 A | 6/1989 | Arroyo | |
| 4,838,282 A | 6/1989 | Strasser et al. | |
| 4,863,072 A | 9/1989 | Perler | 222/390 |
| 4,869,403 A * | 9/1989 | Bruning | 222/327 |
| 4,874,366 A | 10/1989 | Zdeb et al. | 604/518 |
| 4,900,546 A | 2/1990 | Posey-Dowty et al. | |
| 4,915,688 A | 4/1990 | Bischof | 604/83 |
| 4,921,479 A | 5/1990 | Grayzel | |
| 4,929,238 A | 5/1990 | Baum | |
| 4,966,601 A | 10/1990 | Draenert | |
| 4,969,888 A | 11/1990 | Scholten et al. | |
| 4,986,814 A | 1/1991 | Burney et al. | |
| 4,994,029 A | 2/1991 | Rohrbough | 604/88 |
| 5,014,717 A | 5/1991 | Lohrmann | |
| 5,015,101 A | 5/1991 | Draenert | |
| 5,041,120 A | 8/1991 | McColl et al. | 606/99 |
| 5,108,404 A | 4/1992 | Scholten et al. | |
| 5,112,354 A | 5/1992 | Sires | |
| 5,158,561 A | 10/1992 | Rydell et al. | 606/113 |
| 5,195,526 A | 3/1993 | Michelson | |
| 5,249,716 A * | 10/1993 | O'Sullivan | 222/568 |
| 5,258,028 A | 11/1993 | Ersek et al. | 623/23.73 |
| 5,265,956 A | 11/1993 | Nelson et al. | |
| 5,282,861 A | 2/1994 | Kaplan | |
| 5,290,260 A * | 3/1994 | Stines | 604/224 |
| 5,290,291 A | 3/1994 | Linden | 606/99 |
| 5,304,141 A | 4/1994 | Johnson et al. | 604/158 |
| 5,304,586 A | 4/1994 | Hammesfahr et al. | |
| 5,336,263 A | 8/1994 | Ersek et al. | |
| 5,336,699 A | 8/1994 | Cooke et al. | |
| 5,341,816 A | 8/1994 | Allen | |
| 5,344,232 A | 9/1994 | Nelson et al. | |
| 5,346,495 A | 9/1994 | Vargas, III | |
| 5,361,806 A | 11/1994 | Lalikos et al. | 138/109 |
| 5,367,002 A | 11/1994 | Huang et al. | |
| 5,372,583 A | 12/1994 | Roberts et al. | |
| 5,376,094 A | 12/1994 | Kline | 606/113 |
| 5,376,123 A * | 12/1994 | Klaue et al. | 623/23.19 |
| 5,398,483 A * | 3/1995 | Smith et al. | 53/474 |
| 5,415,474 A | 5/1995 | Nelson et al. | |
| 5,431,654 A | 7/1995 | Nic | |
| 5,451,406 A | 9/1995 | Lawin et al. | |
| 5,456,267 A | 10/1995 | Stark | |
| 5,458,579 A | 10/1995 | Chodorow et al. | 604/165 |
| 5,476,102 A | 12/1995 | Como et al. | 600/585 |
| 5,476,880 A | 12/1995 | Cooke et al. | |
| 5,487,725 A | 1/1996 | Peyman | 604/22 |
| 5,496,284 A | 3/1996 | Waldenburg | 604/191 |
| 5,507,813 A | 4/1996 | Dowd et al. | |
| 5,514,137 A * | 5/1996 | Coutts | 606/62 |
| 5,527,298 A | 6/1996 | Vance et al. | |
| 5,558,136 A | 9/1996 | Orrico | |
| 5,571,182 A | 11/1996 | Ersek et al. | |
| 5,571,282 A | 11/1996 | Earle | 366/139 |
| 5,574,075 A | 11/1996 | Draenert | |
| 5,591,171 A | 1/1997 | Brown | |
| 5,595,186 A | 1/1997 | Rubinstein et al. | 600/567 |
| 5,599,305 A | 2/1997 | Hermann et al. | 604/95.04 |
| 5,599,315 A | 2/1997 | McPhee | |
| 5,603,701 A * | 2/1997 | Fischer | 604/211 |
| 5,620,414 A | 4/1997 | Campbell, Jr. | 604/22 |
| 5,637,087 A | 6/1997 | O'Neil et al. | 604/82 |
| 5,647,856 A | 7/1997 | Eykmann et al. | 604/181 |
| 5,650,108 A | 7/1997 | Nies et al. | 264/122 |
| 5,653,730 A | 8/1997 | Hammerslag | |
| 5,658,332 A | 8/1997 | Ducheyne et al. | |
| 5,658,350 A * | 8/1997 | Carbone | 623/23.19 |
| 5,660,186 A | 8/1997 | Bachir | |
| 5,660,210 A | 8/1997 | Ikeda et al. | 138/126 |
| 5,676,146 A | 10/1997 | Scarborough | |
| 5,681,317 A | 10/1997 | Caldarise | 606/93 |
| 5,681,872 A | 10/1997 | Erbe | |
| 5,697,536 A | 12/1997 | Eggers et al. | 606/114 |
| 5,702,446 A | 12/1997 | Schenck et al. | 623/23.55 |
| 5,718,707 A | 2/1998 | Mikhail | 606/94 |
| 5,788,463 A | 8/1998 | Chan | 417/63 |
| 5,788,702 A | 8/1998 | Draenert | |
| 5,792,478 A | 8/1998 | Lawin et al. | |
| 5,795,922 A | 8/1998 | Demian et al. | |

| | | |
|---|---|---|
| 5,797,679 A | 8/1998 | Grulke et al. |
| 5,800,405 A | 9/1998 | McPhee |
| 5,824,087 A * | 10/1998 | Aspden et al. ............... 606/94 |
| 5,827,305 A | 10/1998 | Gordon ...................... 606/159 |
| 5,830,188 A | 11/1998 | Abouleish .................. 604/158 |
| 5,857,995 A | 1/1999 | Thomas et al. ............... 604/22 |
| 5,873,855 A | 2/1999 | Eggers et al. ............... 604/114 |
| 5,876,116 A | 3/1999 | Barker et al. ............. 366/182.3 |
| 5,885,238 A | 3/1999 | Stevens et al. ............ 604/6.14 |
| 5,902,839 A | 5/1999 | Lautenschlager et al. ... 523/115 |
| 5,925,051 A | 7/1999 | Mikhail ........................ 606/94 |
| 5,925,056 A | 7/1999 | Thomas et al. ............. 606/130 |
| 5,928,468 A * | 7/1999 | Tolson ........................ 156/578 |
| 5,951,160 A | 9/1999 | Ronk ......................... 366/130 |
| 5,961,211 A | 10/1999 | Barker et al. ............. 366/182.3 |
| 5,984,897 A | 11/1999 | Petersen et al. ............ 604/187 |
| 5,997,485 A | 12/1999 | Ahmadzadeh ............. 600/567 |
| 5,997,512 A | 12/1999 | Shaw ......................... 604/195 |
| 6,016,845 A | 1/2000 | Quigley et al. ............. 138/125 |
| 6,019,747 A | 2/2000 | McPhee |
| 6,019,765 A * | 2/2000 | Thornhill et al. ............. 606/94 |
| 6,019,776 A | 2/2000 | Preissman et al. .......... 606/185 |
| 6,024,480 A | 2/2000 | Seaton et al. ............... 366/139 |
| 6,033,105 A | 3/2000 | Barker et al. ............. 366/182.3 |
| 6,033,411 A | 3/2000 | Preissman .................... 606/99 |
| 6,039,084 A | 3/2000 | Martucci et al. ............ 138/137 |
| 6,042,262 A | 3/2000 | Hajianpour |
| 6,080,115 A | 6/2000 | Rubinstein .................. 600/567 |
| 6,080,801 A | 6/2000 | Draenert et al. |
| 6,086,543 A | 7/2000 | Anderson et al. ........... 600/567 |
| 6,086,569 A | 7/2000 | Schweizer .................. 604/227 |
| 6,132,400 A | 10/2000 | Waldenburg ................ 604/191 |
| 6,176,607 B1 | 1/2001 | Hajianpour |
| 6,200,289 B1 * | 3/2001 | Hochman et al. ............. 604/67 |
| 6,217,566 B1 * | 4/2001 | Ju et al. ....................... 604/526 |
| 6,217,581 B1 | 4/2001 | Tolson |
| 6,241,734 B1 | 6/2001 | Scribner et al. ............... 606/93 |
| 6,248,110 B1 | 6/2001 | Reiley et al. .................. 606/93 |
| 6,277,112 B1 | 8/2001 | Underwood et al. .......... 606/32 |
| 6,280,456 B1 | 8/2001 | Scribner et al. ............. 606/192 |
| 6,309,420 B1 | 10/2001 | Preissman ................. 623/16.11 |
| 6,348,055 B1 | 2/2002 | Preissman |
| 6,361,504 B1 | 3/2002 | Shin ........................... 600/562 |
| 6,383,190 B1 | 5/2002 | Preissman .................... 606/94 |
| 6,416,484 B1 | 7/2002 | Miller et al. ................. 600/564 |
| 6,425,887 B1 | 7/2002 | McGuckin et al. .......... 604/272 |
| 6,468,279 B1 | 10/2002 | Reo ............................. 606/79 |
| 6,554,803 B1 | 4/2003 | Ashman ...................... 604/218 |
| 6,571,992 B2 * | 6/2003 | Pierson et al. ............... 222/390 |
| 6,572,256 B2 | 6/2003 | Seaton et al. ............... 366/139 |
| 6,575,919 B1 | 6/2003 | Reiley et al. ................ 600/567 |
| 6,582,446 B1 | 6/2003 | Marchosky ................. 606/167 |
| 6,595,958 B1 | 7/2003 | Mickley ................. 604/164.01 |
| 6,602,248 B1 | 8/2003 | Sharps et al. ................. 606/32 |
| 6,613,054 B2 | 9/2003 | Scribner et al. ............... 606/93 |
| 6,662,969 B2 | 12/2003 | Peeler et al. .................... 222/1 |
| 6,676,664 B1 | 1/2004 | Al-Assir ....................... 606/94 |
| 6,679,886 B2 | 1/2004 | Weikel et al. ................. 606/79 |
| 6,712,794 B2 | 3/2004 | Kust et al. ................... 604/224 |
| 6,770,079 B2 | 8/2004 | Bhatnagar et al. ............ 606/94 |
| 6,780,170 B2 | 8/2004 | Fago et al. .................. 604/150 |
| 6,783,515 B1 | 8/2004 | Miller |
| 6,786,885 B2 * | 9/2004 | Hochman et al. ............. 604/67 |
| 6,793,660 B2 | 9/2004 | Kerr et al. ..................... 606/93 |
| 6,875,219 B2 | 4/2005 | Arramon et al. .............. 606/92 |
| 6,945,954 B2 * | 9/2005 | Hochman et al. ............. 604/67 |
| 7,008,433 B2 | 3/2006 | Voellmicke et al. ........... 606/93 |
| 7,018,089 B2 | 3/2006 | Wenz et al. ................. 366/130 |
| 7,077,832 B2 | 7/2006 | Fleischmann ............... 604/304 |
| 7,081,122 B1 | 7/2006 | Reiley et al. ................ 606/185 |
| 2002/0188300 A1 | 12/2002 | Arramon et al. .............. 606/93 |
| 2003/0236506 A1 | 12/2003 | Schofield et al. ............ 604/272 |
| 2004/0068242 A1 | 4/2004 | McGuckin ................... 604/272 |
| 2004/0073139 A1 | 4/2004 | Hirsch et al. ................ 600/564 |
| 2004/0193171 A1 | 9/2004 | DiMauro et al. .............. 606/93 |
| 2004/0215202 A1 | 10/2004 | Preissman .................... 606/94 |
| 2005/0070915 A1 | 3/2005 | Mazzuca et al. .............. 606/93 |
| 2005/0119650 A1 | 6/2005 | Sanders et al. ................ 606/32 |
| 2006/0164913 A1 | 7/2006 | Arramon ..................... 366/139 |
| 2006/0266372 A1 | 11/2006 | Miller et al. ................. 128/898 |

FOREIGN PATENT DOCUMENTS

| | | |
|---|---|---|
| DE | 42 19 563 A1 | 12/1993 |
| DE | 4413520 A1 | 10/1995 |
| EP | 0261182 A1 | 3/1988 |
| EP | 938368 | 9/1999 |
| GB | 1488975 | 10/1977 |
| WO | WO 92/04924 A1 | 4/1992 |
| WO | WO 97/04657 A1 | 2/1997 |
| WO | WO 99/02214 A1 | 1/1999 |
| WO | 99/13272 | 3/1999 |
| WO | 99/18865 | 4/1999 |
| WO | 99/18866 | 4/1999 |
| WO | WO 99/49819 A1 | 10/1999 |
| WO | 2004/073500 | 9/2004 |
| WO | 2005/053510 | 6/2005 |
| WO | 2006/066239 | 6/2006 |
| WO | 2006/071785 | 7/2006 |
| WO | 2006/079106 | 7/2006 |

OTHER PUBLICATIONS

Cotten et al. (1996). "Preoperative percutaneour injection of methyl methacylate and N-butyl cyanoacrylate in vertebral hemangiomas," Am. J. Neuroradiol 17:137-142.

Cybulski. (1989) "Methods of surgical stabilization for metastatic disease of the spine," Neurosurgery 25(2):240-252.

Deramond et al. (1990) "Percutaneous vertebroplasty with methylmethacrylate: technique, method, results," Radiology 117(supp.):352.

Dierks et al. (1992) "Treatment of an infected mandibular graft using tobramycin-impregnated methylmethacrylate beads: Report of a case," J. Oral Maxillofac Surg 50:1243-1245.

Galibert et al. (1987). "Note preliminaire sur le traitement des angiomes vertebraux par vertebroplastie acrylique percutanee," Neurochirurgie 33:166-168. (Partial summary translation included.).

Goode and Reynolds. (1992). "Tobramycin-impergnated methylethacrylate for mandible reconstruction," Arch Otolaryngol Head Neck Surg 118:201-204.

Harrington. (1986). "Anterior decompression and stabilization of the spine as a treatment for vertebral collapse and spinal cord compression from metastatic malignancy," Clin. Orthopaedics and Related Research pp. 177-197.

Kaemmerlen et al. (1989). "Veertebroplastie percutanee dans le traitement des metastases," J. Radiol. 70(10):558-562. (Partial summary translation included.).

McLaughlin et al. (1973). "Blood clearance and acute pulmonary toxicity of methylmethacrylate in dogs after simulated arthroplasty and intravenous injection," J. of Bone and Joint Surg 55-A(8):1621-1628.

Nicola and Lins. (1987). Vertebral hemangioma: Retrograde embolization-Stabilization with methyl methacrylate,: Surg Neurol 27:481-486.

O'Donnel et al. (1994). "Recurrence of giant-cell tumors of the long bones after curettage and packing with cement," J. of Bone and Joint Surg 76-A(12):1827-1833.

Persson et al. (1984). "Favourable results of acrylic cementation for giant cell tumors," Acta Orthop Scand 55:209-214.

Phillips et al. (1971). "Cardiovascular effects of implanted crylic bone cement," British Medical Journal 3:460-461.

Shapiro. (1991) Cranioplasty, vertebral body replacement, and spinal fusion with tobramycin-impregnated methylemethacrylate, Neurosurgery 28(6):789-791.

Stringham et al. (1994). "Percutaneous transpedicular biopsy of the spine," Spine 19(17):1985-1991.

Sundaresen et al. (1985). Treatment of neoplastic epidural cord compression by vertebral body resection and stabilization,: J Neurosurg. 63:676-684.

Wang et al. (1984). "Safety of anterior cement fixation in the cervical spine: In vivo study of dog spine," So. Medical J. 77(2):178-179.

Weill, A. et al. (1996). "Spinal Metastases: Indications for and Results of Percutaneous Injection of Acrylic Surgical Cement," Radiology 199(1):241-247.

U.S. Appl. No. 09/276,062, filed Mar. 24, 1999, Howard Preissman.

U.S. Appl. No. 10/310,354, filed Dec. 4, 2002, Scott Miller.

U.S. Appl. No. 11/369,662, filed Mar. 6, 2006, Scott Miller.

Al-Assir et al, "Percutaneous Vertebroplasty: A Special Syringe for Cement Injection", Am J. Neuroradiol., 21:159-61, Jan. 2000.

Cardinal Health 200, Inc.'s Invalidity Contentions, Filarski et al, pp. 1-65, Nov. 26, 2007.

Claims Chart: Al-Assir and Hasegawa Applied to U.S. Patent No. 6,383,190, pp. 1-25, Nov. 26, 2007.

Claims Chart: Al-Assir and Ju Applied to U.S. Patent No. 6,348,055, pp. 1-17, Nov. 26, 2007.

Claims Chart: Al-Assir Applied to U.S. Patent No. 7,048,743, pp. 1-28, Nov. 26, 2007.

Claims Chart: Coutts, Al-Assir and Ju Applied to U.S. Patent No. 6,348,055, pp. 1-17, Nov. 26, 2007.

Claims Chart: Fischer, Al-Assir and Hasegawa Applied to U.S. Patent No. 6,383,190, pp. 1-27, Nov. 26, 2007.

Claims Chart: Fischer, Al-Assir and Hasegawa Applied to U.S. Patent No. 7,048,743, pp. 1-29, Nov. 26, 2007.

Claims Chart: Jacklich, Al-Assir and Hasegawa Applied to U.S. Patent No. 6,383,190, pp. 1-25, Nov. 26, 2007.

Claims Chart: Jacklich, Al-Assir and Hasegawa Applied to U.S. Patent No. 7,048,743, pp. 1-30, Nov. 26, 2007.

Claims Chart: LeVeen, Al-Assir and Hasegawa Applied to U.S. Patent No. 6,383,190, pp. 1-25, Nov. 26, 2007.

Claims Chart: LeVeen, Al-Assir and Hasegawa Applied to U.S. Patent No. 7,048,743, pp. 1-28, Nov. 26, 2007.

Claims Chart: Nies and Al-Assir Applied to U.S. Patent No. 6,231,615, pp. 1-7, Nov. 26, 2007.

Claims Chart: Nies Applied to U.S. Patent No. 6,309,420, pp. 1-17, Nov. 26, 2007.

Claims Chart: Pulpdent Pressure Syringe, Al-Assir and Hasegawa Applied to U.S. Patent No. 7,048,743, pp. 1-27, Nov. 26, 2007.

Claims Chart: Slooff, Al-Assir and Hasegawa Applied to U.S. Patent No. 6,383,190, pp. 1-25, Nov. 26, 2007.

Claims Chart: Slooff, Al-Assir and Hasegawa Applied to U.S. Patent No. 7,048,743, pp. 1-29, Nov. 26, 2007.

Claims Chart: Stines, Al-Assir and Hasegawa Applied to U.S. Patent No. 6,383,190, pp. 1-27, Nov. 26, 2007.

Claims Chart: Stines, Al-Assir and Hasegawa Applied to U.S. Patent No. 7,048,743, pp. 1-29, Nov. 26, 2007.

Claims Chart: Pulpdent Pressure Syringe, Al-Assir and Hasegawa Applied to U.S. Patent No. 6,383,190, pp. 1-26, Nov. 26, 2007.

Gangi et al, "Percutaneous Vertebroplasty Guided by a Combination of CT and Fluoroscopy", Am J. Neuroradiol., 15:83-86, Jan. 1994.

Haas et al, "A Characterization of Polymethylmethacrylate Bone Cement", J. Bone and Joint Surg., 57-A(3):380-91, Apr. 1975.

Krakow et al., "Efficient Endodontic Procedures with the Use of the Pressure Syringe", Dental Clinics of North America, 387-99, Jul. 1965.

Saha et al., "Mechanical properties of bone cement: A review", J. Biomed. Materials Red. 18:435-62, 1984.

Slooff, "A cement syringe", Acta Orthopaedica Belgica 35(1):1012-4, Feb. 1969.

Unknown author, "Part Four—Pulpdent Root Canal Sealer and Pulpdent Pressure Syringe" 222-9, date unknown.

PCT International Search Report and Written Opinion for PCT/US06/02625, 8pgs, Mailed Dec. 13, 2007.

"Syringe". Merriam-Webster Online dictionary, retrieved from the internet <URL:www.m-w.com> retrieved on Jan. 28, 2007.

"Acrylic glass". Wikipedia online, retrieved from the Internet <URL: www.wikipedia.com> retrieved on Jan. 28, 2007.

Unknown author, "Trocar Entry Control", Research Disclosure No. 38938, pp. 570-574, Sep. 1996.

KyphX® Express™ System, Kyphon Inc., 4 pgs, 2004.

KyphX® One-Step™ Osteo Introducer® System, Kyphon Inc., 2 pgs, 2004.

Reusable Syringes and Application Systems, <http://www.henkesasswolf.de/e/main_rs.htm>, Aug. 21, 2002.

PCT Notification of the Internatinal Search Report for PCT/US98/21572, 6 pgs, Mailed Feb. 18, 1999.

PCT Notification of the Internatinal Search Report for PCT/US98/21662, 8 pgs, Mailed Feb. 18, 1999.

PCT Notification of the International Preliminary Examination Report for PCT/US98/21662, 8pgs, Mailed Nov. 30, 1999.

PCT Notification of the International Preliminary Examination Report for PCT/US98/21572, 15gs, Mailed Mar. 13, 2000.

PCT Notification of the International Search Report and Written Opinion for PCT/US05/46829, 6pgs, Mailed Oct. 18, 2006.

PCT Notification of the International Preliminary Examination Report for PCT/US99/06470, 4 pgs, Mailed Aug. 9, 2000.

PCT Written Opinion for PCT/US99/06470, 4 pgs, Mailed Feb. 1, 2000.

PCT Notification of the International Search Report for PCT/US99/06470, 6 pgs, Mailed Jul. 2, 1999.

PCT Notification of the International Search Report for PCT/US99/23006, 6 pgs, Mailed Feb. 11, 2000.

Written Opinion of the International Searching Authority for PCT/US04/04538, 3 pgs, Mailed Nov. 22, 2004.

PCT International Search Report for PCT/US04/04538, 1 pg, Mailed Nov. 22, 2004.

PCT International Search Report for PCT/US04/39486, 1 pg, Mailed Feb. 22, 2006.

PCT Written Opinoin for PCT/US04/39486, 3 pgs, Mailed Feb. 22, 2006.

PCT International Search Report for PCT/US05/46070, 1 pg, Mailed Sep. 7, 2006.

PCT Preliminary Report on Patentability for PCT/US05/46070, 3 pgs, Mailed Jun. 28, 2007.

* cited by examiner

HIGH PRESSURE APPLICATOR

CROSS REFERENCE TO RELATED APPLICATIONS

This application is a continuation of application Ser. No. 10/039,892, filed Oct. 26, 2001, now abandoned, which is a divisional of Application Ser. No. 09/409,934, filed Sep. 30, 1999, now U.S Pat. No. 6,383,190, which is a continuation in part of application Ser. No. 09/053,108, filed Apr. 1, 1998, now abandoned, entitled "Pressure Applicator for Hard Tissue."

TECHNICAL FIELD

The present invention relates to instruments for more accurately controlling the placement of implant material thereof, during surgical procedures for the repair of hard tissue by injection of hard tissue implant materials. Procedures for such repair include hip augmentation, mandible augmentation, and particularly vertebroplasty, among others.

BACKGROUND ART

Polymethylmethacrylate (PMMA) has been used in anterior and posterior stabilization of the spine for metastatic disease, as described by Sundaresan et al., "Treatment of neoplastic epidural cord compression by vertebral body resection and stabilization." *J Neurosurg* 1985;63:676-684; Harrington, "Anterior decompression and stabilization of the spine as a treatment for vertebral collapse and spinal cord compression from metastatic malignancy." *Clinical Orthodpaedics and Related Research* 1988;233:177-197; and Cybulski, "Methods of surgical stabilization for metastatic disease of the spine." *Neurosurgery* 1989;25:240-252.

Deramond et al., "Percutaneous vertebroplasty with methyl-methacrylate: technique, method, results [abstract]." *Radiology* 1990;117 (suppl):352, among others, have described the percutaneous injection of PMMA into vertebral compression fractures by the transpedicular or paravertebral approach under CT and/or fluoroscopic guidance. Percutaneous vertebroplasty is desirable from the standpoint that it is minimally invasive, compared to the alternative of surgically exposing the hard tissue site to be supplemented with PMMA or other filler.

The general procedure for performing percutaneous vertebroplasty involves the use of a standard 11 gauge Jamshidi needle. The needle includes an 11 gauge cannula with an internal stylet. The cannula and stylet are used in conjunction to pierce the cutaneous layers of a patient above the hard tissue to be supplemented, then to penetrate the hard cortical bone of the vertebra, and finally to traverse into the softer cancellous bone underlying the cortical bone.

A large force must be applied by the user, axially through the Jamshidi needle to drive the stylet through the cortical bone. Once penetration of the cortical bone is achieved, additional downward axial force, but at a reduced magnitude compared to that required to penetrate the cortical bone, is required to position the stylet/tip of the cannula into the required position within the cancellous bone. When positioned in the cancerous bone, the stylet is then removed leaving the cannula in the appropriate position for delivery of a hard tissue implant material to reinforce and solidify the damaged hard tissue.

A syringe is next loaded with polymethyl methacrylate (PMMA) and connected to the end of the cannula that is external of the patient's body. Pressure is applied to the plunger of the syringe to deliver the PMMA to the site of damaged bone at the distal end of the cannula. Because in general, 10 cc syringes are only capable of generating pressures of about 100-150 psi, this places a limitation on the viscosity of the PMMA that can be effectively "pushed through" the syringe and cannula and fully delivered to the implant site. Of course, the use of a small barrel syringe, e.g., a 1 cc syringe, enables the user to generate higher driving pressures. For example, pressures of 1000 psi and possibly as high as 1200-1500 psi (depending upon the strength of the user and the technique) may be generated using a 1 cc syringe. A serious limitation with the use of a 1 cc syringe, however, is that it will not hold a large enough volume to complete the procedure in one step or "load" and must be reloaded several times to complete the procedure, since, on average, about 3.5 cc of implant material per side of the vertebral body are required for an implantation procedure. This makes the procedure more complicated with more steps, and more risky in that the polymerization of the implant material causes it to become increasingly more viscous during the additional time required for reloading. Another problem with a 1 cc syringe is lack of control, as high pressures are, generated in a "spike-like" response time and are not continuously controllable.

A viscous or paste-like consistency of PMMA is generally believed to be most advantageous for performing percutaneous vertebroplasty. Such a consistency insures that the implant material stays in place much better than a less viscous, more liquid material. Leakage or seepage of PMMA from the vertebral implant site can cause a host of complications some of which can be very serious and even result in death. For example, Weil et al. reported cases of sciatica and difficulty in swallowing which were related to focal cement leakage, *Radiology* 1996;Vol 199, No. 1, 241-247. A leak toward the distal veins poses an even more serious risk, since this can cause a pulmonary embolism which is often fatal.

In addition to the viscosity effects noted above that require greater pressure to deliver hard implant tissue material, when such material (like PMMA) is implanted percutaneously, the need to inject it through a relatively narrow needle or cannula also greatly increases the need for a high pressure driver. Still further, implantation of PMMA into a relatively closed implantation site (e.g., trabecular bone) further increases the resistance to flow of the PMMA, at the same time increasing the pressure requirements of the driver. Thus, there is a need for a high pressure applicator that has enough storage capacity to perform a complete implantation procedure without having to reload the device in the midst of the procedure, and which is consistently controllable, for an even, constant application of pressure during delivery of the entirety of the implant material.

Attempts have been made to increase the ability to apply pressure to drive PMMA to the vertebral implant site by providing a smaller barrel syringe, but this holds less volume and must be refilled once or several times to deliver enough volume of PMMA to the site. Since there is a limited amount of time to work with PMMA before it begins to polymerize or set up, this type of procedure is more difficult to successfully complete within the allotted time, and thus poses an additional risk to the success of the operation.

Accordingly, there exists a need for an improved apparatus and procedure for controllably applying higher pressures to a source of implant material, and particularly to hard tissue implant materials, to successfully implant the material at the desired location in a single batch, for the performance of vertebroplasty and particularly, percutaneous vertebroplasty.

DISCLOSURE OF THE INVENTION

The present invention includes a high pressure applicator for driving the delivery of a flowable tissue implant material. A first column having an inner wall, an outer wall, a first open end and a second substantially closed end is provided with an orifice through the substantially closed end for passage implant materials therethrough under high pressure. A second column is drivably engageable with the first column to generate fluid pressure within at least the first column. Preferably, a e wall portion of the second column is drivably engageable with one of an inner and outer wall of the first column A handle is preferably fixedly attached or integral with the first column and may extend radially from the first column to provide a user a mechanical advantage upon grasping it.

At least one sealing element may be provided to interface with the inner wall of the first column, to enhance the generation of pressure in the first column. A handle is also preferably integrally formed with or affixed to the second column and may extend radially therefrom to provide a user a mechanical advantage upon grasping it.

In one embodiment of the invention, threading is provided on an outer wall of the first column. The second column is substantially hollow, having an open first end, a closed second end and threading on an inner wall thereof. The threading on the second column in this embodiment is engageable with the threading on the first column to provide a driving force for driving the second column with respect to the first column. The second column may include an extension integrally formed with or affixed thereto and optionally having an end portion extending from the open end of the second column. The extension is adapted to be inserted through the open end of the first column and form a substantial pressure seal with the inner wall of the first column.

Additionally, at least one sealing element may be provided at or near the end portion of the extension to form or enhance a pressure seal with the inner wall of the first column. The sealing element(s) may be an Q-ring(s), a grommet(s) or the like.

In another embodiment, a plunger element is provided which is adapted to be inserted within the first and second columns. The plunger element has a first end portion and a second end portion, where the first end portion is adapted and configured to closely fit within the inner wall of the first column to form a pressure seal therewith. At least one sealing element may be provided for the first end portion to form and/or enhance a pressure seal between the inner wall and the plunger element A handle may be integrally formed with or affixed to the second column, to optionally extend radially therefrom, to provide the user a mechanical advantage upon grasping it. The plunger element may further be provided with at least one frictional element mounted to the second end portion and adapted to form a disengageable friction fit with the second column at or near the closed end of the second column.

A high pressure applicator according to the present invention may include threading on at least a portion of the inner wall of the first column, and the second column may have threading on at least a portion of an external wall thereof such that the threading of the external wall is engageable with the threading on at least a portion of the inner wall of the first column to provide a driving mechanism for driving the second column with respect to the first column. The interengaging threads may be formed to closely fit to form a pressure seal therebetween upon their engagement. At least one sealing element may be mounted to an end portion of the second column and adapted to form or enhance a pressure seal with the inner wall thereby forming or enhancing the pressure seal between the first and second columns. The sealing element(s) may comprise an O-ring(s), a Teflon wrap(s), or the like. A handle may be integrally formed with or affixed to the second column to extend radially therefrom, to provide a user a mechanical advantage upon grasping it.

Various portions of a pressure applicator may be sized to provide sufficient mechanical advantage to enable the application of pressures up to about 3000 or 4000 psi by hand. The mechanical advantage of an applicator is determined in large part by handle size, the bore size of the first column, and the mechanical advantage of the engagement mechanism. With regard to the engaging threads used as an engagement mechanism, manufacturing and material considerations, and the diameter on which to place the threads will determine the thread pitch which may be used. This in tam determines the mechanical advantage of this engagement mechanism. Where a greater mechanical advantage is desired, a finer thread pitch will provide the same. To achieve this, the diameter of threaded sections of the first and second columns may be decreased. Alternately, a finer pitch thread may be used on a relatively larger diameter section by changing material or manufacturing procedure (such as cutting the threads into the respective members rather than molding the pieces as is presently preferred). In all, a pressure applicator produced according to the present invention is a balancing of various design goals relating to performance and cost.

In an arrangement where the threads cover only a portion of the external wall, the remainder of this wall of the second column is left relatively smooth. In this arrangement, only a portion of the inner wall of the first column has threads, and the remainder of the inner wall is left substantially smooth. The relatively smooth end portion of the second column has a reduced diameter section having an outside diameter less than an inside diameter of the threads on said inner wall, to allow assembly or interfitting of the two columns. An enlarged section extending from the reduced diameter portion closely fits with the substantially smooth inner wall to form a pressure seal therewith. The first column in this arrangement additionally includes a hinged or removable section adapted to swing open or be removed therefrom to allow insertion of the second column. At least one sealing element, which may be an O-ring or the like, may be mounted to the end portion of the second column to form or enhance a pressure seal therewith.

In yet another embodiment, the first column is substantially hollow and comprises an inside wall, an open first end and a closed second end, and a barrel portion of a syringe is received therein. A plunger portion of the syringe is received within a second column. The applicator may include threading on an outer wall of the first column and threading on an inner wall of the second column, where the threads are engageable with one another to provide a driving force for driving the plunger portion with respect to the barrel portion. A handle may be integrally formed with or affixed to the second column and optionally extend radially therefrom and to provide the user a mechanical advantage upon grasping it.

An end of the barrel portion of the syringe may abut against the substantially closed end of the first column and an end of the plunger portion may abut against the closed end of said second column, such that driving of the second column with respect to the first column provides a driving force for advancing the plunger portion within the barrel portion. The barrel portion may further include a wing or flanged portion adjacent an open end thereof. The first column may have a first portion adjacent the open end, a second portion adjacent the substantially closed end and a transitional portion joining the first and second portions, where the first portion has an inside diameter larger than an inside diameter of the second portion. In this case, the transitional portion may be adapted to abut against the wing or flanged portion, to provide additional or alternative support for the barrel portion as the plunger portion is being advanced with respect thereto.

Alternatively, a high pressure applicator according to the present invention may include a syringe having a barrel portion and a plunger portion, where the syringe barrel is received within the first column where threading is provided on at least a portion of the inner wall of the first column and on at least a portion of an external wall of the second column. In this embodiment of the invention, the second column includes an end adapted to abut an end of the plunger portion of the syringe and threading of the external wall is engageable with the threading on at least a portion of the inner wall to provide a driving force. The operation and variations of this embodiment are substantially like those described directly above.

A method of preparing a high pressure applicator for driving the delivery of a flowable tissue implant material for use is disclosed to include: providing an applicator having a first column having an inner wall, an outer wall, a first open end and a second substantially closed end having an orifice therethrough, and a second column drivably engageable with the first column to generate a pressure within the first column; loading the flowable tissue implant material into the first column; engaging the second column with the first column to enclose the tissue implant material; and advancing the second column toward the first column to generate a pressure for driving the flowable tissue material through the orifice.

The second column may include a plunger adapted to form a pressure seal with the inner wall of the first column, in which case the engagement of the second column with the first column includes introducing the plunger into the tissue implant material in such a way to avoid the introduction of air bubbles or other compliant matter together with the implant material to be delivered to a patient. Advancement of the second column toward the first column generates a pressure for driving the flowable tissue material through the orifice, which may be at least 1000 psi. Optionally, a substantially non-compliant tube may be connected to the orifice prior to advancing the second column toward the first column to generate a pressure for driving the flowable tissue material through the orifice.

As another option, a substantially non-compliant tube may be connected to the orifice after advancing the second column toward the first column to generate a pressure for driving the flowable tissue material through the orifice, thereby purging the orifice prior to connecting the substantially noncompliant tube. In either case, the substantially noncompliant tube may be, but is not necessarily prefilled (e.g., with saline or implant material) prior to connecting it to the orifice.

Loading of the first column with implant material may be done in such a way as to slightly overfill the first column to form a meniscus created by surface tension of the implant material. In this case, the engagement of the first and second columns then may include introducing a plunger element into the implant material and then driving the plunger via the advancement of the second column.

A method of preparing a high pressure applicator for driving the delivery of a flowable tissue implant material for use is provided which includes: providing an applicator containing at least 5 cc of tissue implant material therein; and actuating the applicator to generate an internal pressure of at least 1000 psi which acts as a driving force to force a flow of the implant material from the applicator. The pressure generated may be at least 1500 psi, at least 2000 psi, at least 2500 psi or up to about 3000 psi.

Further, the method is described as torquing a first portion of the applicator with respect to a second portion of the applicator actuator to generate the driving force. The applicator may be provided to contain at least 7.5 cc of tissue implant material, up to 10 cc of tissue implant material, or even up to about 15 cc of tissue implant material therein. A preferred embodiment currently holds about 9 cc of implant material.

BRIEF DESCRIPTION OF THE DRAWINGS

Each of the following figures diagrammatically illustrates aspects of the present invention. No aspect shown is intended to be limited to the expression pictured.

BEST MODE FOR CARRYING OUT THE INVENTION

The present invention substantially improves the delivery of hard tissue implant sites to the targeted zone of implantation, and is especially well suited for percutaneous deliveries. The present invention substantially reduces several of the risk factors associated with the performance of percutaneous vertebroplasty. Additionally, the present invention enables an increase in an upper acceptable viscosity value of the implant to be delivered because of the increase in the amount of pressure available for controllably driving the delivery.

Figure 19:
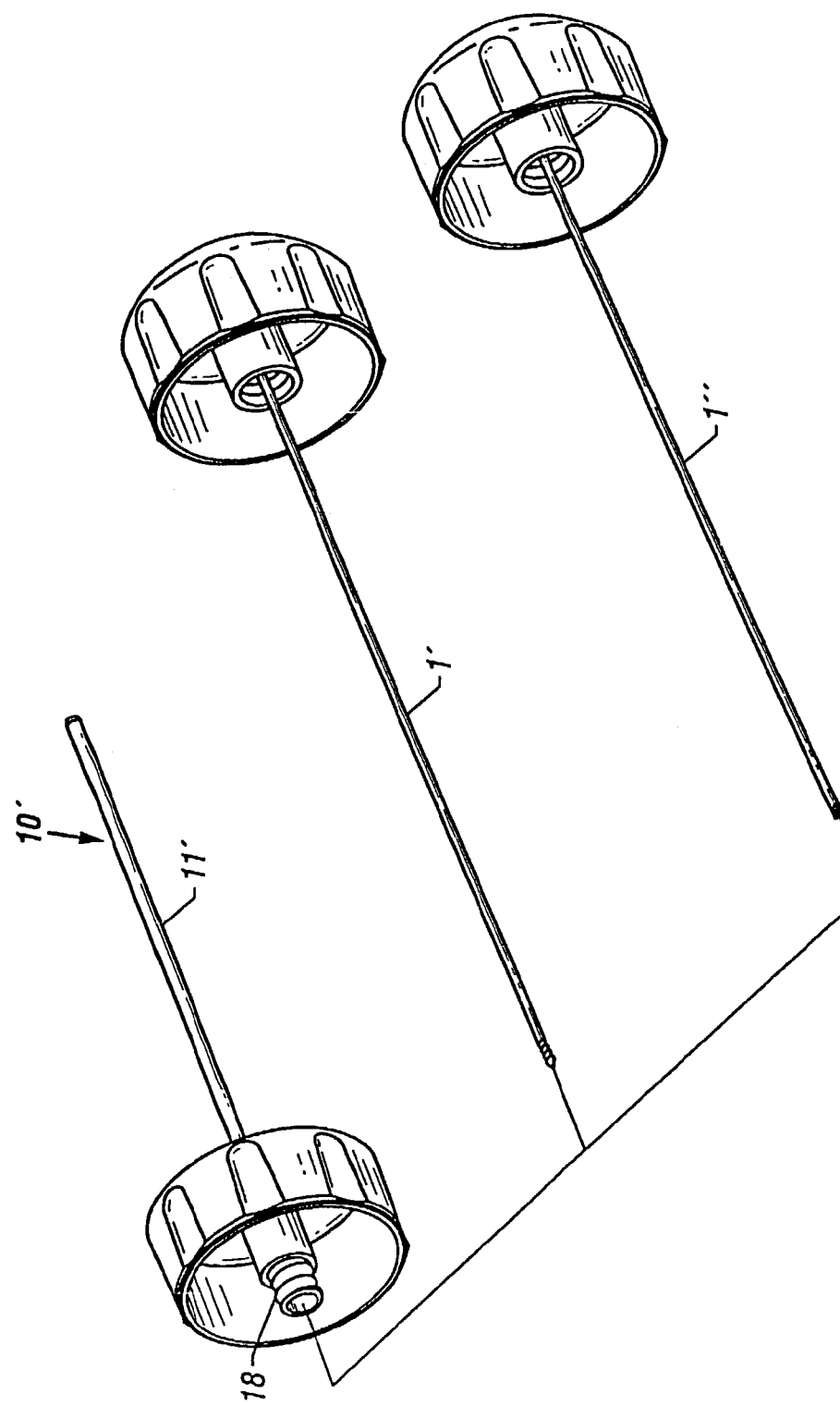
FIG. 19 shows a cannula and two types of stylets useable with the present invention and indicates the manner in which they are assembled.

An example of a procedure for performing percutaneous vertebroplasty is illustrated in FIGS. 1-6. Beginning with FIG. 1, an example of the use of depth guided instruments will now be described. For a more detailed description of various depth-guided instruments that can be used for accessing the cortical bone, the reader is directed to copending application Ser. No. 08/950,382, filed on Oct. 14, 1997, entitled "Precision Depth Guided Instruments for Use in Vertebroplasty"; and copending application Ser. No. 08/949,839, filed on Oct. 14, 1997, entitled "Precision Depth Guided Instruments for Use in Vertebroplasty". Both applications, numbered Ser. Nos. 08/950,832 and 08/949,839 are hereby incorporated by reference in their entireties. A currently preferred stylet 1' and cannula 10', and an optional direction guiding stylet 1" are shown in FIG. 19. A detailed description of these devices and their uses are disclosed in a co-owned application filed concurrently herewith, entitled "Precision Instruments for Use in Vertebroplasty". The aforementioned application 09/409,948 is hereby incorporated by reference in its entirety.

Figure 1:
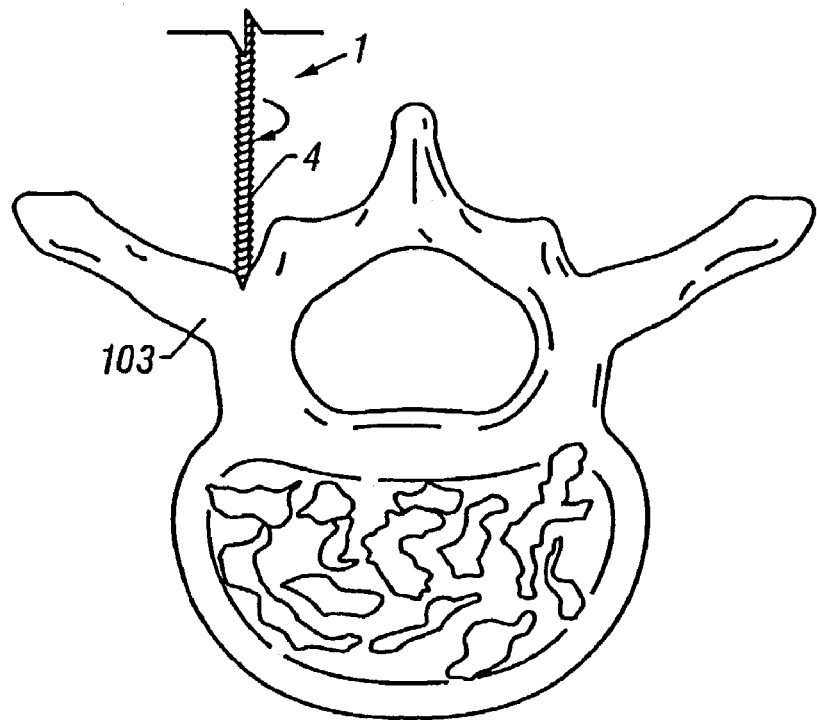
FIG. 1 shows of an initial phase of insertion of a stylet into an implant site;.
Figure 2:
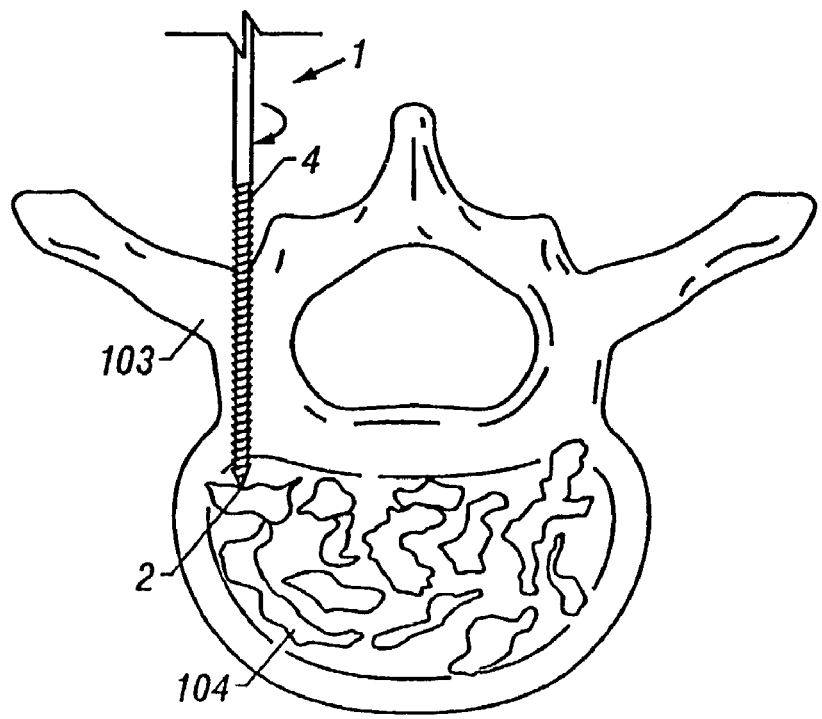
FIG. 2 shows the stylet having penetrated the cortical bone and approaching cancellous bone.

In the example shown in FIG. 1, a stylet 1 is provided which has a length that is more than sufficient to span the distance from the epidermis of a patient to the cancellous bone tissue in the vertebra, in the preferred configuration. Typically the length of the stylet would be about three inches or greater, but lesser lengths may also be employed as well, depending on the size of the patient. Of course, if other hard tissues are to be accessed, the length of the stylet can be readily modified without departing from the inventive features of the present invention.

The stylet 1 is preferably made of a surgical grade of stainless steel, but other known equivalent biocompatible metals and materials may be used for the same purpose. Ideally, the stylet, or at least a distal end thereof, will be radiopaque so that it can be monitored using fluoroscopy, CT or other imaging techniques during the procedure to help determine the depth and location of the penetration.

Figure 3:
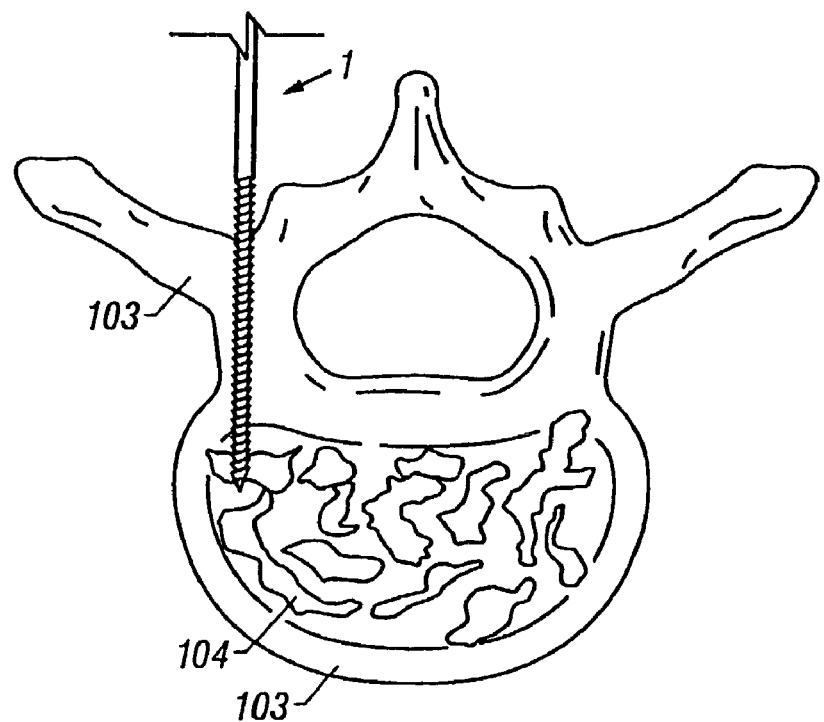
FIG. 3 shows the stylet having reached the desired site of implantation.

A first or distal end of the stylet 1 ends in a point 2 which is sharp and adapted to penetrate hard tissue when axially loaded. Extending from the tip 2 are self-tapping threads 4. The self-tapping threads 4 provide an advantage in that once the tip 2 has penetrated the cortical bone (e.g., see FIG. 2), the operator of the stylet can then proceed to advance the stylet by torquing the stylet, which engages the self-tapping threads 4 in the cortical bone 103 and begins to screw the stylet 1 into the cortical bone 103. Rotation of the stylet 1 is continued, to advance the stylet into the bone, while monitoring the advancement with some type of imaging technique, e.g., fluoroscopy or equivalent. It is noted that actual fluoroscopic views are generally from a perspective other than that shown in the Figures. However, for ease and clarity of illustration, the Figures depict a transverse sectional view of the vertebra as the instruments enter the vertebral body. Advancement is continued until the tip 2 reaches the site at which it is desired to deliver the implant material. Usually this site is in the cancellous bone as shown in FIG. 3, but could be anywhere within the bone where there is osteoporosis, or a fracture or other defect or trauma.

A cannula 10 is provided which includes an elongated tubular structure 11 to be positioned in the cancellous bone or other implantation site for delivery of PMMA or other bone implant material therein. The tubular structure 11 of the cannula 10 is preferably made of a surgical grade of stainless steel, but may be made of known equivalent materials, similarly to the stylet 1 discussed above. Preferably, at least a distal end of the tubular structure is radiopaque. The tubular structure 11 has an inside diameter which is only slightly larger than the outside diameter of the stylet 1, so that the cannula may effortlessly pass axially over the stylet, while at the same time being supported and guided by the stylet. A first or distal end 12 of the cannula is preferably (but not necessarily) beveled or tapered to ease the penetration of the cannula through the cutaneous and soft tissues, and especially through the hard tissues.

Surrounding the second end of the tubular structure 11 (or 11' in FIG. 19) is a connector 18 (FIGS. 6, 19) for linking the cannula 10, 10' with a pressure applicator according to the present invention, for supplying the PMMA or other implantable material that is to be injected via tubular structure 11,11'. Preferably, connector 18 is a Luer-lock type of connector, but other known connecting mechanisms may be successfully interchanged, e.g., a flat bottom threaded hole, a conventional threaded hole, a threads and locking nut arrangement, etc.

Figure 4:
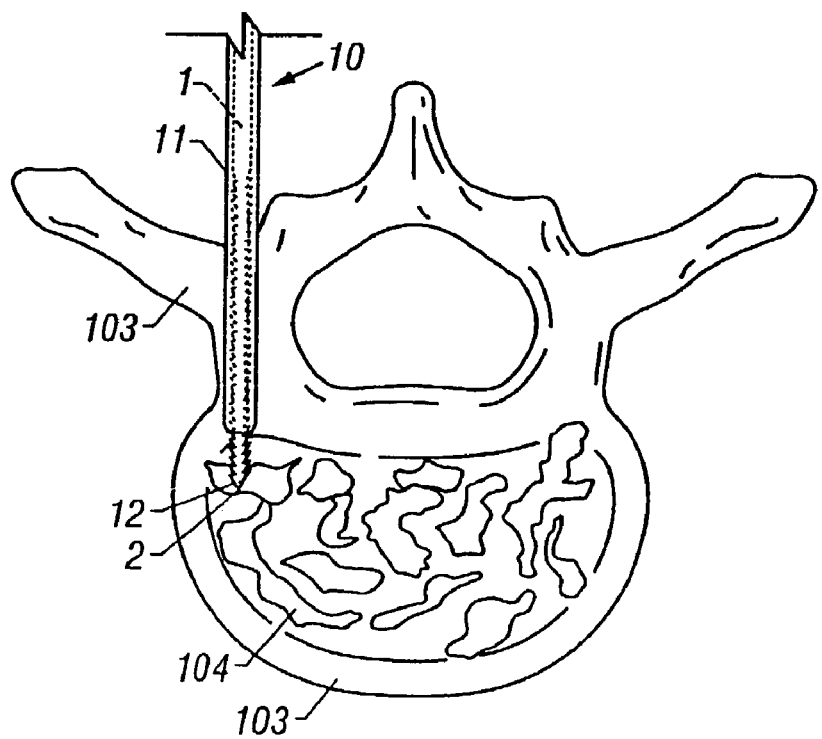
FIG. 4 shows the positioning of a cannula by guiding it along the stylet.
Figure 5:
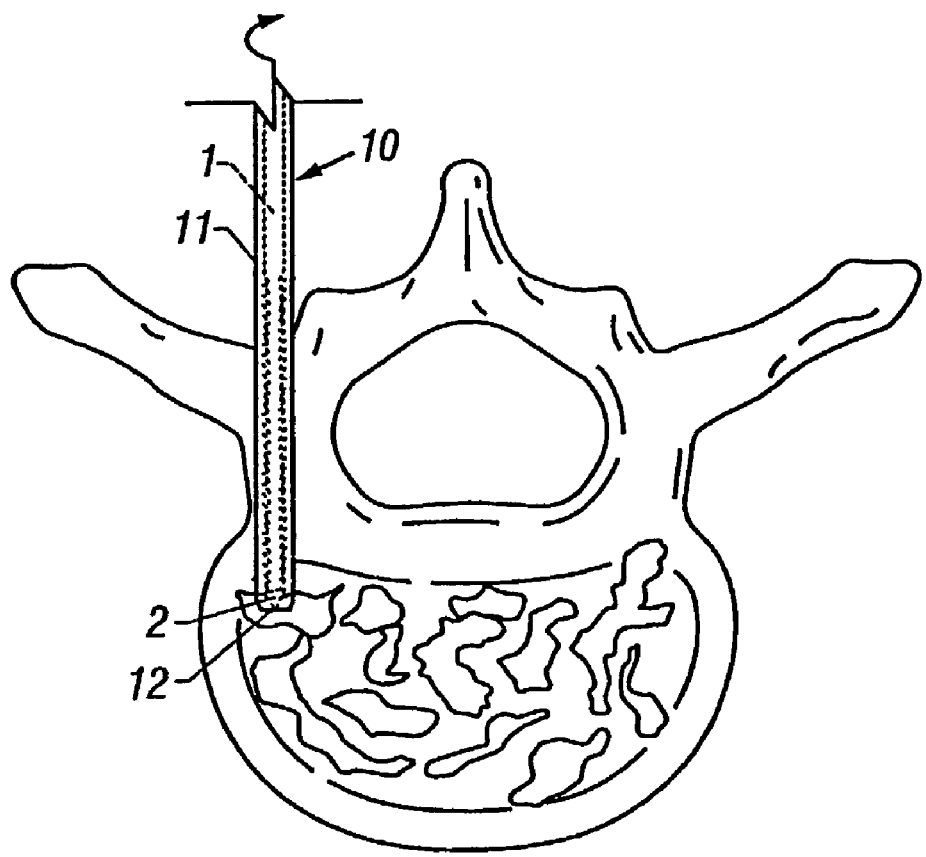
FIG. 5 shows the cannula in position at the desired site of implantation, with the stylet still in position.

As shown in FIGS. 4-5, the cannula 10 is advanced over the stylet, until visualization of the process indicates that the end of the cannula 12 is substantially even with the tip of the stylet 2, whereby it is confirmed that the cannula is properly positioned for delivery of the implant material. On the other hand, the cannula 10' and stylet 1' are advanced together, which is currently the preferred method of insertion. Next the stylet 1 is removed from the site, either by reverse rotation or by simply withdrawing it. At the same time the cannula 10 is maintained in position to be readied for delivery of the implant material.

Figure 6:
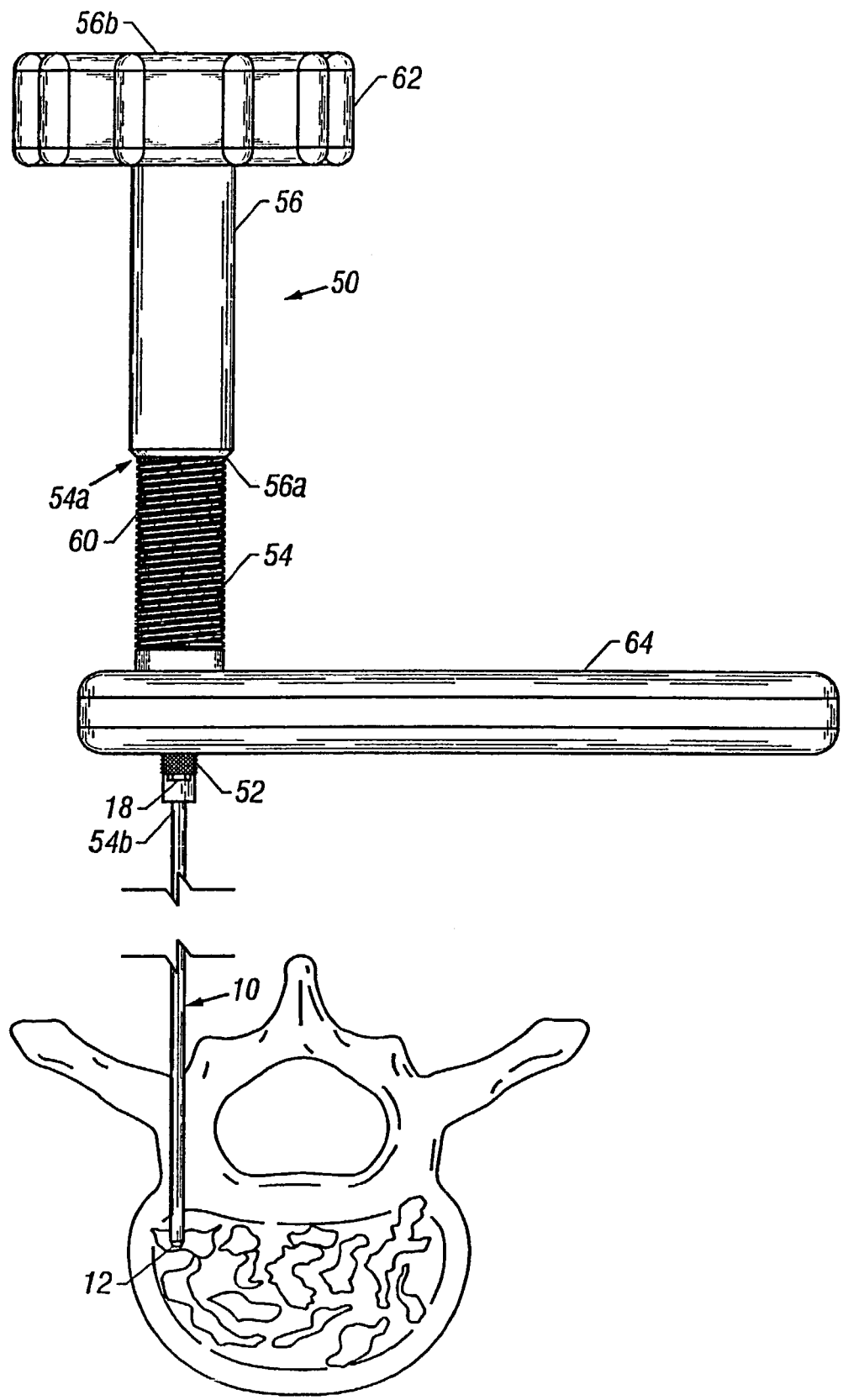
FIG. 6 shows a stage after the stylet has been removed and a high pressure applicator has been mounted to the cannula.

A pressure applicator 50 according to the present invention is next mounted to the connector 18 at the end of cannula 10, as shown in FIG. 6. The pressure applicator 50 is provided with a fitting 52 which is designed to form a pressure tight connection with the connector 18. As mentioned above, the preferred type of connection is a Luer-lock type connection, but alternative, equivalent types of connectors may be employed. The pressure applicator further includes a first column 54 for receiving and containing implant material. The first column 54 is open at one end 54a for receiving the material. At the other end 54b of the first column is a much smaller opening or orifice which ends with the connector or transfer fitting 52 or into which the connector or transfer fitting is mounted or placed (e.g., by threading, bonding, or the like).

A second column 56 is provided for overfitting first column 54 and providing a pressure seal therewith. Preferably, the second column 56 has interior threads 58 as shown in phantom in the exploded view of FIG. 7. The interior threads 58 mate or engage with exterior threads 60 provided on the first column 54. However, other equivalent types of drivable engaging arrangements, e.g., a ratchet and pawl arrangement, interior threading arrangement in the first column, or other equivalent arrangements could be used in place of the mating threads, so long as adequate force is able to be generated and maintained between the two columns for providing the driving pressure for the implant material.

Column 56 is open at end 56a for receiving the first column 54 therein. At the opposite end 56b, column 56 is closed to enable a generation of pressure within the two columns as they are moved toward one another and column 56 passes over column 54. Preferably, at least one sealing element 57 (e.g., a square, round or other type of O-ring, grommet, wrap of material or the like) is provided to maintain a high pressure fitting between the columns 54 and 56 to better enable a high pressure driving force to be generated for driving implant material from within the device through the opening 54b. The sealing element(s) 57 may also be provided integrally with the column 55, e.g., by flaring out the column material to provide an interference fit, or the like. Since implant materials to be used in the invention (e.g. PMMA) are often very viscous, a high pressure capacity ensures that even thicker or more viscous mixes of implant material may be driven by the applicator 50.

An advantageous implant material that may be used with the high pressure applicator of the present invention is a PMMA bone cement including contrast agents and/or tracer particles. Aspects of such a material are described in U.S. patent application Ser. No. 08/950,256, "Enhanced Visibility Materials For Implantation In Hard Tissue" by Preissman, filed Oct. 14, 1997. Contrast radiographic powder or particles of any typical material and of a size between 0.5μ to 1000μ may be included.

To form the requisite seal to drive the implant material, a separate "sealing" element need not necessarily be provided. However, especially where highly viscous materials are concerned, the O-ring or grommet optionally provided is preferred since it can move on the plunger rotationally and thus even if the plunger is turning with the handle, the seal can move independently.

Figure 7:
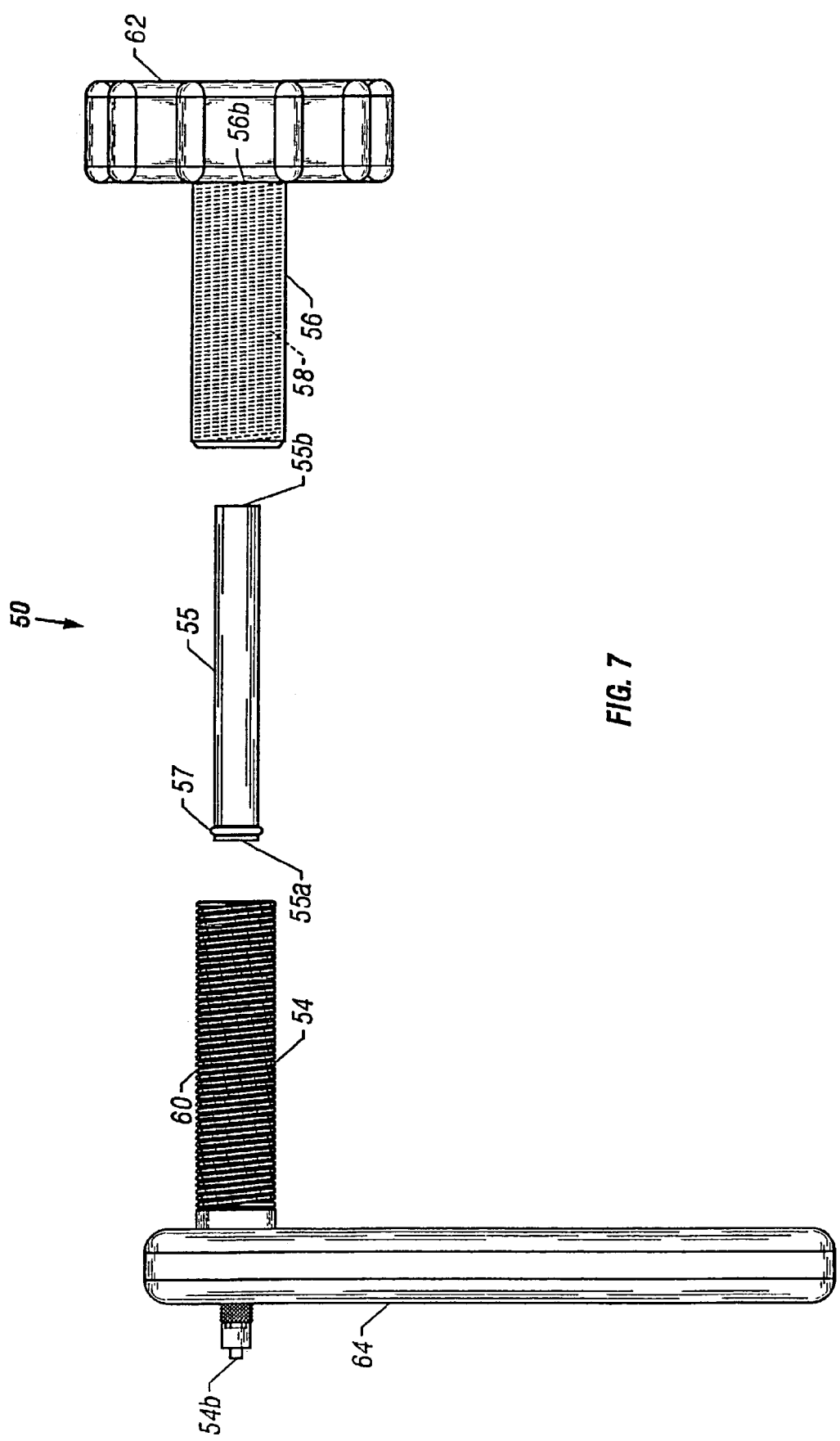
FIG. 7 shows the high pressure applicator used in FIG. 6.

Returning to the applicator in the embodiment of FIG. 7, however, a plunger element 55 is provided to be slidably driven by the first column 56 into the second column 54. At least one O-ring 57 or equivalent sealing mechanism is mounted near a first end 55a of the plunger element 55 to provide a friction fit between the plunger element 55 and the interior wall of the first column 54. In use, the plunger element 57 is "started" in the end 54b of the column 54, by inserting a small length of the plunger element 57 to an extent which is at least enough to seat the O-ring 57 with the inner wall of the column 54. Next the second column 56 is initially connected with the column 54 by mating the threads 58 and 60. Subsequent torquing of the handle 62 advances the closed end 56b of the column 56 toward the second end 55a of the plunger element 55 until it makes contact therewith Continued torquing of the second column 56 with respect to the first column 54 advances the plunger element 55 against the implant material 66 (not shown in FIG. 7). Sealing element 57, in combination with the advancement of the plunger element 55, generates a pressurized driving force which results in expulsion of the implant material from end 54b of the second column 54.

A handle 62 is mounted on the column 56 to provide additional leverage for driving the column 56 with respect to column 54. In the example shown in FIGS. 6 and 7, the handle 62 is provided at the closed end 56b to provide a greater mechanical advantage for torquing column 56 about its longitudinal axis. Of course, the handle could be provided anywhere along the column 56 so long as it extends the effective radius for torquing about the longitudinal axis. A handle 64 is fixedly attached, molded, or otherwise mounted to the first column 54. The handle 64 may be grasped by the operator and provides leverage against rotation of the first column 54 during driving of the second column 56. Preferably, the handle 64 is in the form of a lever as shown in FIG. 6, but alternative embodiments of the handle may include a circular handle, etc. so long as a sufficient mechanical advantage is provided to the user.

For other types of driving mechanisms, other types of handles might be employed. For example, a lever might extend from the column in an embodiment using a ratchet and pawl type of driving mechanism.

The above described components of the pressure applicator 50 are all preferably formed of amorphous nylon or ABS plastic, with at least column 54 being formed of clear or translucent amorphous nylon. However, any other materials which are durable, sterilizable, biofriendly and chemically compatible with the material to be implanted (e.g., stainless steel) could be readily substituted. As a further example, although polycarbonate is not recommend for implanting PMMA, it may be fully acceptable for use in implanting other types of materials with which it has better chemical compatibility.

Figure 8:
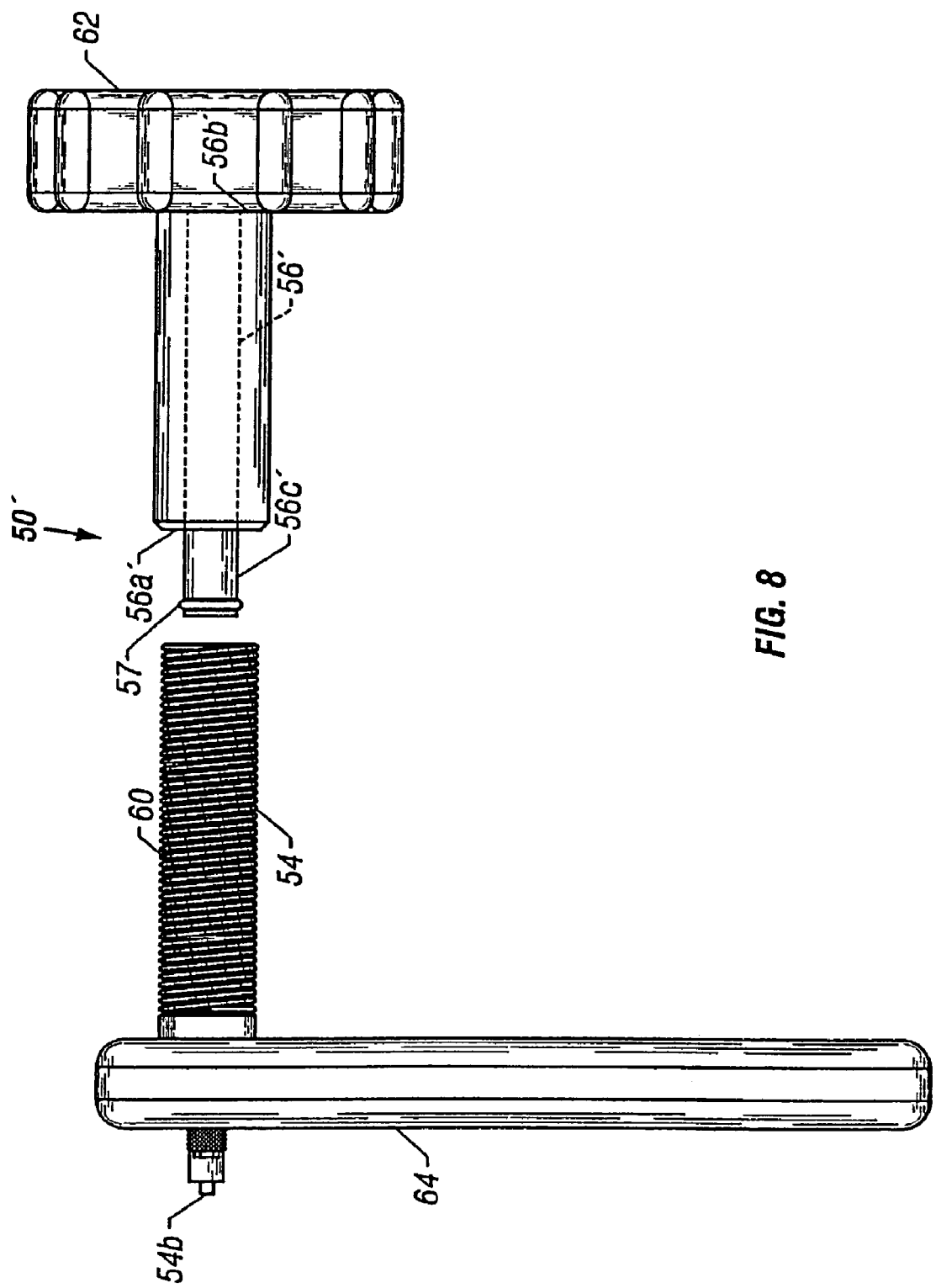
FIG. 8 shows an alternative embodiment of a high pressure applicator according to the present invention.

Although the plunger element 55 is shown as a separate component in the embodiment of FIG. 7, it is noted that this element may be integrally formed with the column 56', as shown in the embodiment of FIG. 8, to form an extension 56c' of the second column 56'. As shown by the phantom lines, the extension 56c' is integrally formed or affixed to the closed end 56b' of the column 56' and extends the length thereof to emerge from the open end and extend therefrom to allow the sealing end and sealing element 57 to be inserted into the column 54, prior to starting the interengagement of threads 58 and 60. Note that threads 58 are not indicated in phantom, or at all, in FIG. 8 for purposes of simplification of the Figure and to allow the phantom lines depicting the extension 56c' more clearly. It is further noted that the extension 56c' does not have to take the form of the plunger 55, but may have a much smaller cross section where it extends from the closed end. For example, the extension 56c' may be formed as a much smaller rod with a first end having the same dimensions as that shown in FIG. 8, to provide a proper seal with the column 54.

Figure 9:
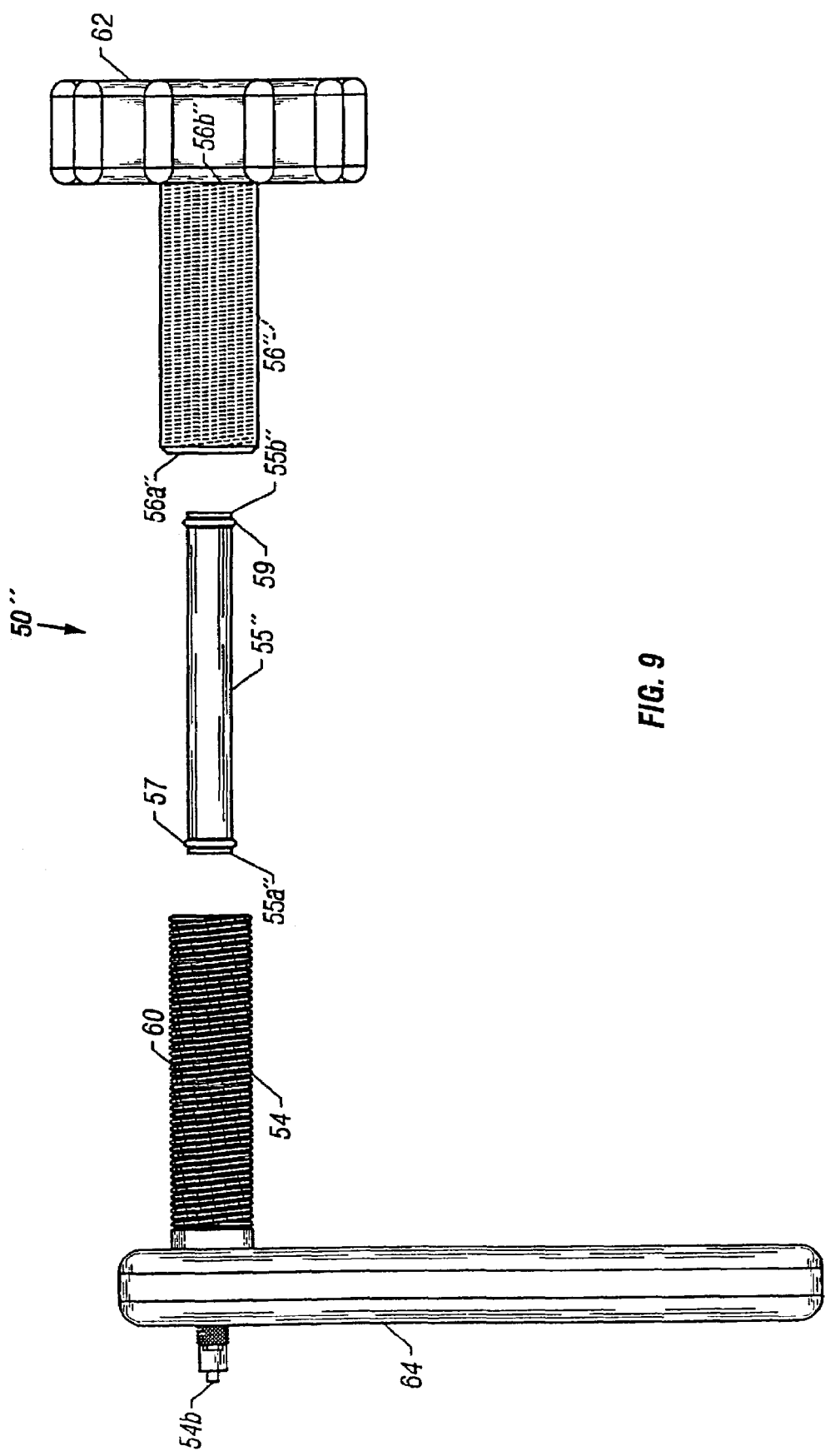
FIG. 9 shows another embodiment of a high pressure applicator according to the present invention.

FIG. 9 shows another embodiment of a pressure applicator 50" according to the present application. Pressure applicator 50" is provided with a plunger element 55" which includes sealing element 57 and frictional element 59, both preferably O-rings, at opposite ends thereof. The sealing and frictional arrangements are not limited to the placement of one O-ring or equivalent but may use two or another multiple of sealing elements. Frictional element 59 is provided to form a friction fit inside the closed end 56b" of the column 56". Thus, the plunger element 55" is inserted into the column 56" initially until the end 55b" bottoms out against the closed end 56b" and the frictional element 59 forms a friction fit with the inner wall of the column 56" adjacent the closed end 56b". The friction fit is sufficient to maintain the plunger element 55" in position within the column 56" even when the column is held vertically, by the handle 62, with the open end 56a" pointing downward.

Additionally, after implant material is loaded into the column 54, and the end 55a" and sealing element 57 are started into the column 54 to seat the sealing element 57 against the inner wall of the column 54, the friction fit between sealing element 57 and column 54, in combination with the friction fit between the sealing element 59 and column 56" act to prevent rotation of the plunger element with respect to the column 54 as the plunger element is advanced into the column by the driving force of the column 56". Specifically the frictional forces between the sealing element 57 and the column 54 are greater than those between the sealing element 59 and the column 56" so that the sealing element 59 slips against the inner wall of the column 56" as the column 56" is torqued to advance both the column 56" and the plunger element 55" with respect to the column 54. By this action, the rotational movement of the closed end 56b" of the column 56" is converted to a solely translational force against driving the plunger element 55". This feature is particularly important when the implant material comprises PMMA, as PMMA is somewhat abrasive if the plunger element 55" and sealing element 57 are allowed to rotate or are driven to, rotate with respect to the column 54, this may allow some of the PMMA to work its way between a portion or all of the sealing element 57 and inner wall of the column 54 where it can act as an abrasive to prematurely degrade the sealing element 57 and/or the wall of the column 54. By eliminating rotation of the sealing element 57 with respect to the inner wall of the column 54 so purely translational or sliding movement occurs upon actuation of the applicator, migration of PMMA between the sealing element 57 and column 54 wall are minimized or eliminated.

The end 55b" and sealing element 59 as shown have dimensions slightly larger than those of the end 55a" and sealing element 57 to account for the slightly larger inside diameter of the column 56" relative to the inside diameter of the column 54. However, it is not necessary to use these dimensions, since a recess (not shown) having a smaller diameter can be formed (by boring, molding or otherwise) into the closed end 56b" so that a smaller end 55b" and sealing element 59 can be employed to form a friction fit therewith.

Figure 23A:
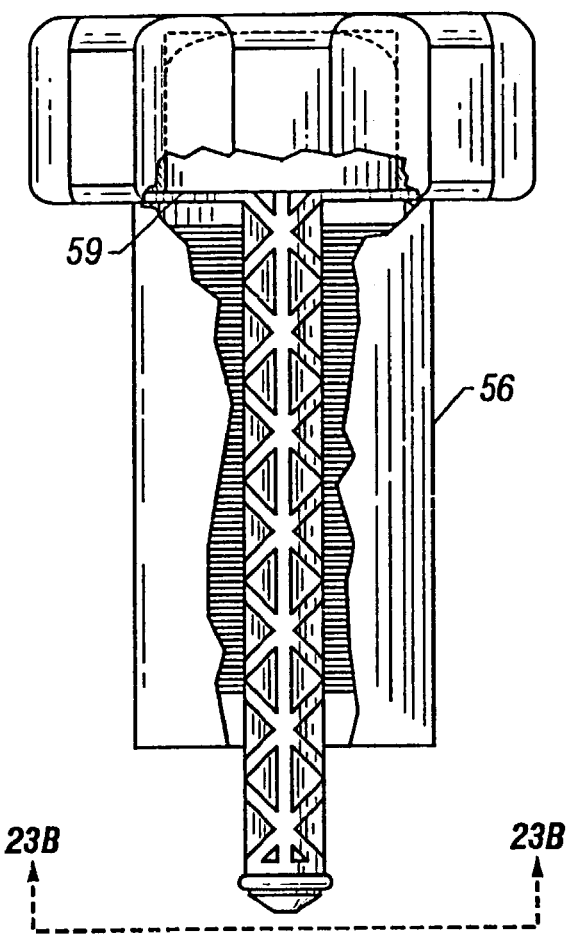
FIG. 23A shows a partially cut away view of a housing member, retainer member and plunger.
Figure 23B:
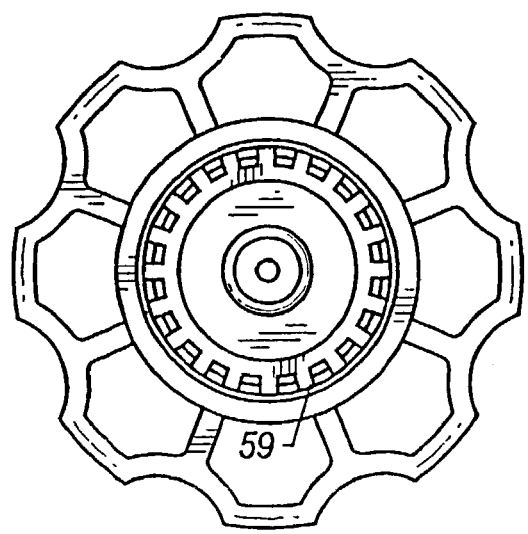
FIG. 23B shows an end view of FIG. 23A.
Figure 23C:
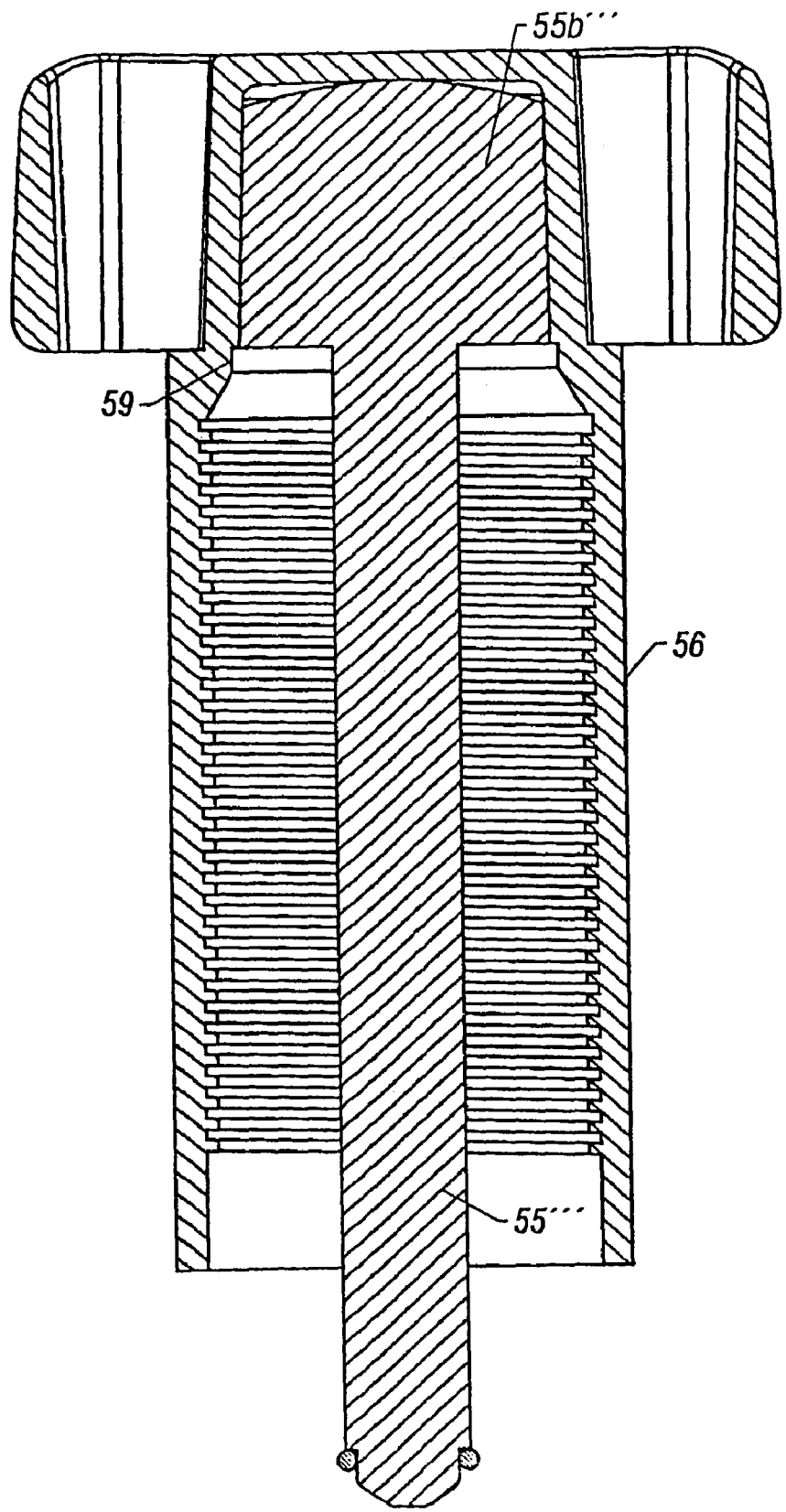
FIG. 23C is a sectional view of FIG. 23A showing the engagement of the plunger with the housing member.

Another variant of a frictional element useable to prevent rotation of the plunger or rod upon actuation of the applicator is pictured in FIGS. 23A-23C. The enlarged base 55b''' of the piston/plunger rod 55''' includes and end 55d having a spherical surface which is free to rotate with respect to the inner end surface 56d of the second column 56. The enlarged base 55b''' is held ill position by the placement of one or more (preferably two) internal retaining rings 59 which engage within a recess in second column 56 and abut the enlarged base 55b''' to substantially prevent translational movement thereof with respect to the second column 56. Thus the rod 55''' will not fall out of the second column 56 when inverted or otherwise jostled, but the rod 55''' is still allowed to turn relative to the column 56.

Figure 10:
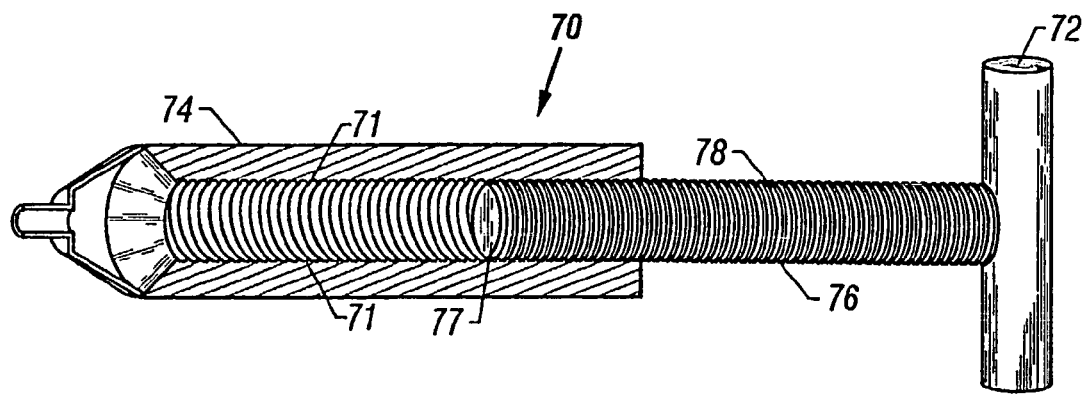
FIG. 10 shows an embodiment of a pressure applicator according to the present invention in which a portion of the column 74 has been cut away to show the relationship between the column or shaft 76 and column 74.

FIG. 10 is a partial sectional view of an embodiment of a pressure applicator 70, according to the present invention, in which a portion of the column 74 has been cut away to show the relationship between the column or shaft 76 and column 74. In this embodiment, column 74 is interiorly threaded with threads 71 which mate with threads 78 on the exterior of column 76. A sealing element 77 (e.g., an O-ring, Teflon wrap (formed by wrapping with Teflon tape, for example) or other equivalent) may be mounted at or near the end of the column 76 to enhance the pressure seal between the columns 76 and 74, although close tolerance threads may be employed to generate sufficient pressure without the use of a sealing element. Although not shown, a handle is also preferably mounted to the column 74 (e.g., similar to the handle 64 described above or to handles described below) to assist the user in developing the torque needed to generate high pressures. A handle 72 is mounted to column 76 to further assist in generating torque.

Figure 11:
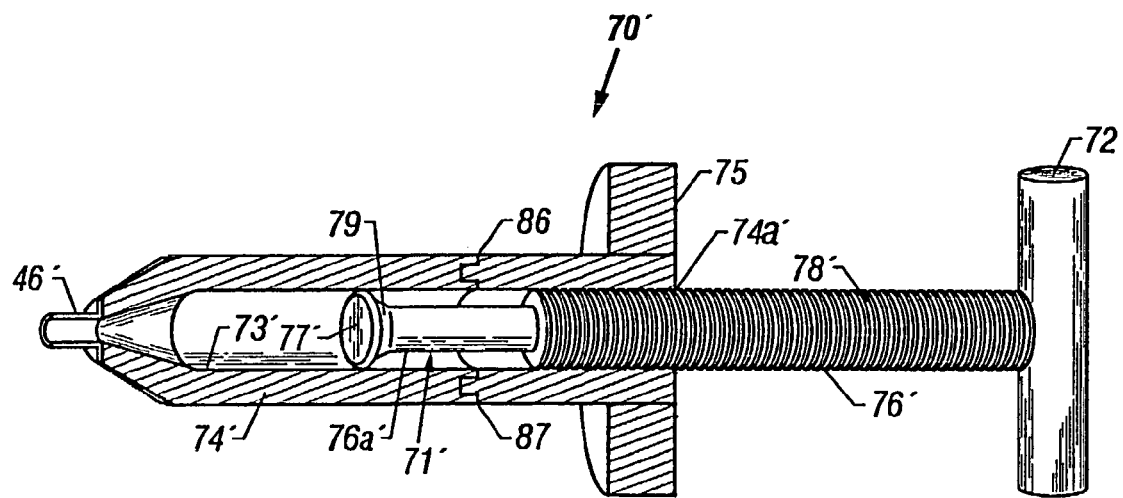
FIG. 11 shows a variation of the pressure applicator in FIG. 10 in which a portion of the column 74' has been cut away to show the relationship between the column or shaft 76' and column 74'.

FIG. 11 is a partial sectional view of a variation of an embodiment of a pressure applicator 70', according to the present invention, in which a portion of the column 74' has been cut away to show the relationship between the column or shaft 76' and column 74'. In this embodiment, the threads 71' are radially inset from the remainder of the inner wall 73' of column 74' which is left smooth. Threads 78' are exteriorly provided on column or shaft 76' which mate with threads 71'. The distal end of shaft 76' is provided with an enlarged portion 79 which closely approximates or mates with the smooth inner wall 73'. A sealing element 77' (e.g., an O-ring, Teflon tape or other equivalent) may be mounted at or near the end of the enlarged portion 79 to enhance the pressure seal between the columns 76' and 74'. A handle 75 is also preferably mounted to the column 74' to assist the user in developing the torque needed to generate high pressures. Although handle 75 is shown mounted to the proximal end of the column 74', it is noted that the handle may also be mounted to the distal end, similar to that described with respect to handle 64 above, or at virtually any location along the length of the column that may be desirable, and still achieve the advantages of enhancing torque generation. Also, the handle 75 may be molded or otherwise formed integrally with the column 74' or, alternatively, may be fixedly mounted to the column 74' (e.g., by bonding, welding, splined or other mechanical arrangement) to provide torque to the column 74' without slipping with respect thereto. A handle 72 is mounted to column 76' to further assist in generating torque.

Figure 12A:
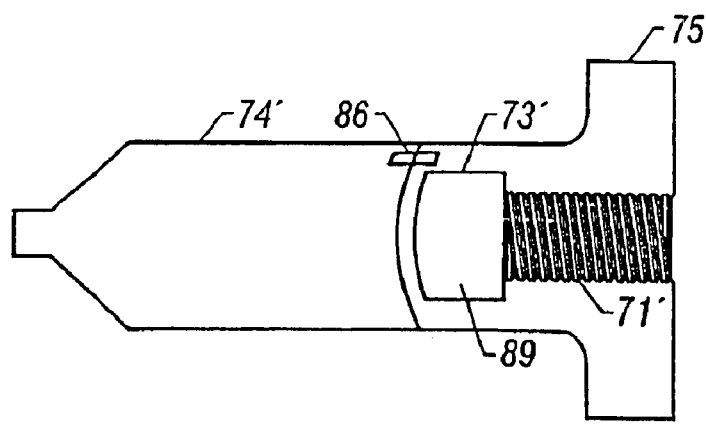
FIG. 12A shows the column 74' in FIG. 11 with an opening formed by removal of a hinged or removable section.
Figure 12B:
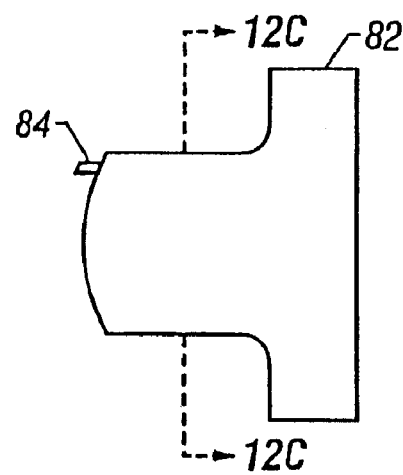
FIG. 12B shows the removable section 82 of column 74'.
Figure 12C:
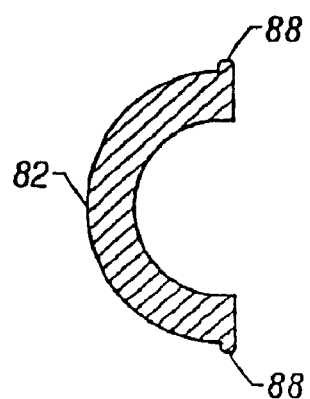
FIG. 12C shows the removable section taken along section line 12C-12C in FIG. 12B.

Column 74' must be provided with an access as shown in FIG. 12A, to allow insertion of the shaft 76', since the outside diameter of the enlarged portion 79' is greater than the diameter of the distal opening 74a' of the column 74'. One example of providing such an access, is to provide a hinged or removable section 82 which may be swung open or removed from the remainder of the column 74' during the insertion of the column 76'. In the example shown in FIGS. 11-12C, section 82 includes a hinge pin 84 which is insertable into a recess 86 in the wall of the remainder of the column 74' for pivoting therewith, or allowing removal of the section altogether. Other types of hinges or movable attachments may be readily substituted for the hinge pin 84 and recess 86 as would be apparent to those of ordinary skill in the art.

One or preferably both edges of the section 82 may be provided with flanges 88 or similar extensions to provide a snap or friction fit with the remainder of the column 74' when the section 82 is installed. Further optionally, the inner wall of the remainder of the column may be provided with a recess or groove 87 to receive the flange or extension 88 to provide a more secure interlock. Additionally or alternatively, the column 74' may be provided with a clamp or tying band (not shown) to surround the section 82 and column 74' and compress the two pieces slightly to maintain them in a secure relationship.

Insertion of the column 76' is performed by first removing or swinging open the section 82 away from the remainder of the column 74'. The proximal portion 76a' of the column 76' has a smaller outside diameter than the threaded portion 78' and is also sufficiently smaller than the inside diameter of the threads 71', so that the enlarged portion 79 can be placed in the space 89 while the proximal portion 76a' clears the threads 71'. The section 82 is then replaced by snapping and/or clamping the same into position against the remainder of the column 74', thereby surrounding the proximal portion 76a' and enlarged portion 79. Threads 78' can then be started with threads 71' to ready the applicator 70' for application of a pressurized driving force.

Figure 13:
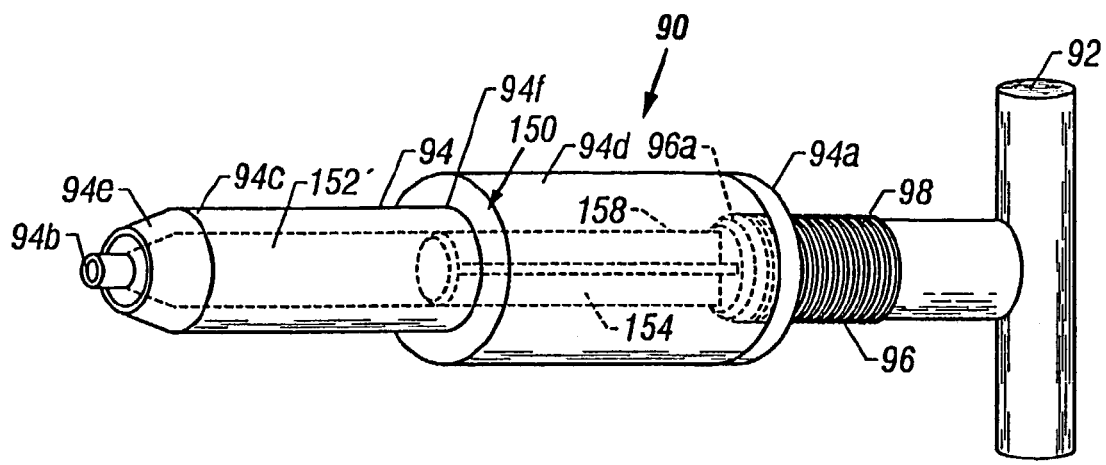
FIG. 13 shows another embodiment of a pressure applicator according to the present invention.

FIG. 13 is a plan view of another embodiment of a pressure applicator 90 according to the present invention. Column 94 is configured and dimensioned to receive a disposable syringe 150 (shown in phantom lines) therein. For example, this embodiment can be used with a 10 cc syringe, thereby enabling much greater pressures to be generated than discussed above. The column 94 can be formed as a two stage column, as shown, having a first inside diameter 94c which is smaller than a second inside diameter 94d. This design allows the barrel 152 of the syringe 150 to be received in the portion 94c and abut against a tapered portion of the column 94e. Additionally, or alternatively, a transition collar 94f which interconnects the varying diameter portions 94c and 94d of the column 94, provides a surface against which the flange or "wings" of the syringe barrel 152 abut. An alternative arrangement could have a column having a single stage or inner diameter which could rely on the tapered region 94e solely for abutment of the syringe barrel 152.

The syringe plunger 154 is received in the larger diameter portion 94d of the column 94 (which, in the alternative arrangement described would be the single stage or diameter). A second column or shaft 96 is externally threaded and external threads are designed to mate with internal threads (not shown) on the interior wall of the column portion 94d. The distal end 96a of column 96 abuts against the end 158 of the syringe plunger 154 upon threading the column 96 into column 94. Further torquing of the handle 92 with respect to the column 94 generates a driving force for translationally advancing the syringe plunger 154 to generate a high pressure driving force. A sealing element (not shown) is preferably mounted at or near the distal end of the syringe plunger 154, as is known in the art, to enhance the pressure generation. Although not shown, a handle is also preferably mounted to the column 94 (e.g., similar to the handle 64 or 75 described above) to assist the user ill developing the torque needed to generate high pressures.

Figure 14:
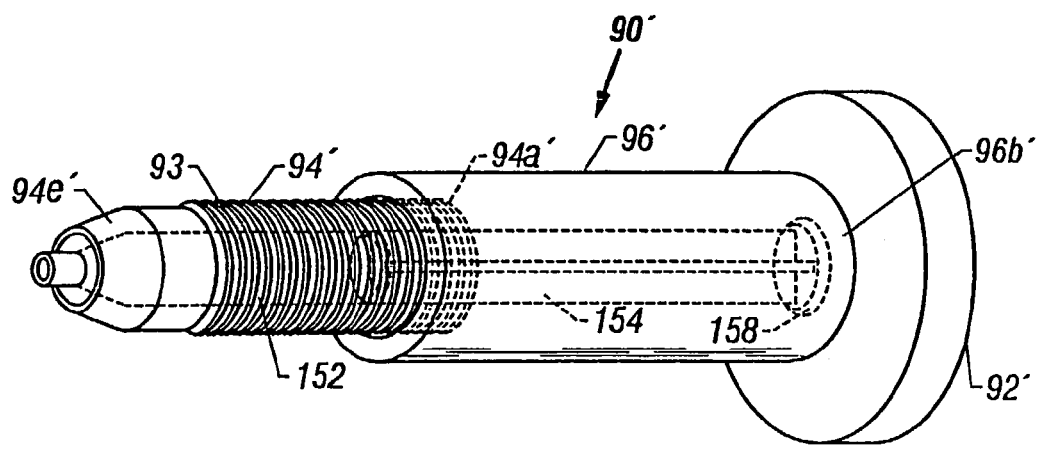
FIG. 14 shows still another embodiment of a pressure applicator according to the present invention.

FIG. 14 is a plan view of another embodiment of a pressure applicator 90' according to the present invention. Column 94' is configured and dimensioned to receive a disposable syringe 150 (shown in phantom lines) therein. The column 94' can be formed as a two stage column, similar to that described above with regard to FIG. 13, but is formed as a single stage or single diameter column in FIG. 14. This design allows the barrel 152 of the syringe 150 to be received in the column 94' and abut against a tapered portion of the column 94e'. The syringe plunger 154 extends from the proximal opening 94a' of the column 94 and is received in the column 96'. Column 96' is internally threaded (threads not shown) and the internal threads are designed to mate with external threads 93 on column 94'. The closed proximal end 96a) of column 96' abuts against the end 158 of the syringe plunger 154 upon receiving the plunger 154 in column 96' and beginning mating of the internal threads of the column 96' with threads 93. Further torquing of the handle 92' with respect to the column 94' generates a driving force for translationally advancing the syringe plunger 154 to generate a high pressure driving force. A sealing element (not shown) is preferably mounted at or near the distal end of the syringe plunger 154, as is known in the art, to enhance the pressure generation. Although not shown, a handle is also preferably mounted to the column 94, (e.g., similar to the handle 64 or 75 described above) to assist the user in developing the torque needed to generate high pressures.

Figure 15:
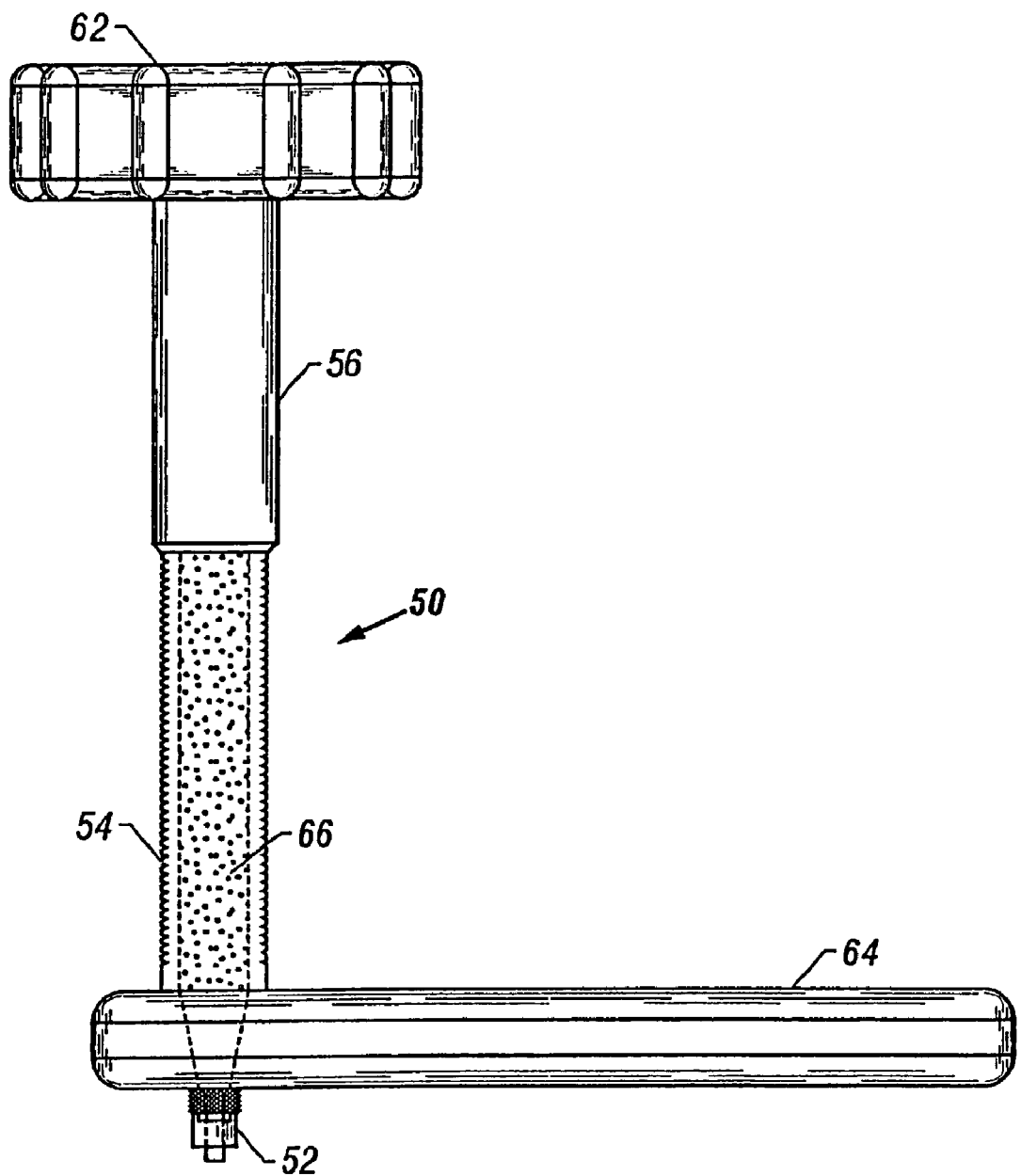
FIG. 15 shows a high pressure applicator after being loaded with a hard tissue implant material and assembled.
Figure 18:
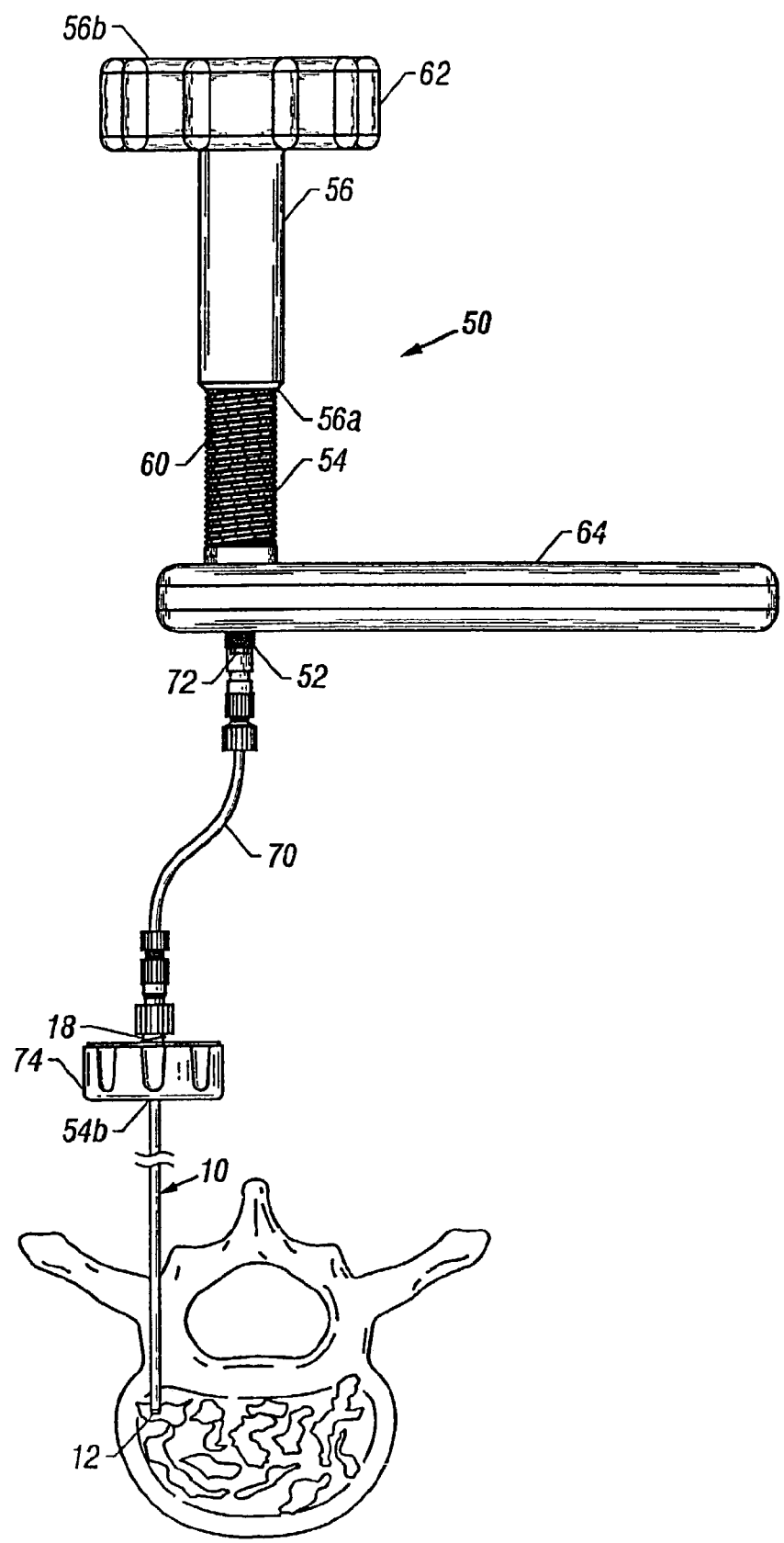
FIG. 18 shows an arrangement for high pressure, substantially noncompliant delivery of an implant material.

In using the pressure applicator according to the present invention to drive a tissue implant material, a tissue implant material, in this example, a hard tissue implant material 66 is loaded into the first column 54 and the second column 56 is connected with the first column 54 in preparation for implantation, see FIG. 15. Although the pressure applicator 50 is shown in FIGS. 6, 15 and 18, it is noted that the principles described with respect thereto are generally applicable to each of the embodiments described herein. Of course, minor variations in procedure may be necessary, e.g., loading the syringe 150 with implant material, rather than the pressure applicator column, when using the embodiments of FIGS. 13 and 14, etc., but the general principles described herein may be applied to any embodiment by those of ordinary skill in the art. Prior to mounting the pressure applicator 50 on the cannula 10, a tissue implant material 66 is loaded into the first column 54 and the second column 56 is connected with the first column 54 in preparation for implantation. Optionally, the introduction of air bubbles can be further substantially reduced or avoided by slightly overfilling the firs column to form a meniscus created by surface tension of the implant material and then introducing the plunger element into the material and driving the plunger into the first column. This optional technique may be used in all of the disclosed embodiments, but may be obviated by the features shown in the embodiments of FIGS. 20-22, as discussed below. The first column is then rotated slightly with respect to the second column until a minimal amount of tissue implant material is expressed from the fitting 52 end, to ensure that no air has been entrapped in the applicator. The cannula 10 is backfilled with saline, tissue implant material 66, or other biocompatible fluid in order to displace the air therefrom. The pressure applicator 50 is then mounted onto the cannula 10 as described above and shown in FIG. 6. The operator next grasps the handle 62 in one hand and the handle 64 in the other and begins to torque the handle 62 while maintaining the handle 64 in its position. When operated as described, the pressure applicator is capable of generating pressures of about 1000 to 3000 psi within the columns, which is a high driving force that is applied to the implantable material 66.

Torquing of the handle 62 with respect to the handle 64 is continued until a sufficient amount of implant material 66 has been delivered to the implant site as verified by an appropriate imaging technique. A variety of endpointing techniques are described in the application Ser. No. 09/409,948 entitled "Precision Instruments for Use in Vertebroplasty", which was incorporated by reference above. Advantageously, the pressure applicator 50 allows a first column 54 which is large enough in volume at least 5 cc, preferably at least 7.5 cc, and more preferably at least 10 cc and up to about 15 cc to contain sufficient implant material for an entire implantation process so that there is no need to refill the column 54 in the midst of a procedure. For uses that require the delivery of larger volumes of implant material, the designs disclosed herein could be enlarged so as to have a capacity up to 25 cc and even upwards of 30 cc. It would further be apparent to those of ordinary skill in the art to modify the designs herein to have capacities even larger than that disclosed should an implantation procedure require larger volumes of material.

A modification of the apparatus described above is shown in FIG. 16. In this embodiment, cannula 10' includes a modified tubular structure design. The first or distal portion 11a of the tubular structure is of the same dimensions as the embodiment of FIGS. 1-6. The second or proximal portion 11b of the cannula 10', however, has a substantially larger diameter than that of the first portion 11a. Preferably, the diameter of second portion 11b is about twice the diameter of the first portion 11a, although any increase in the diameter of the second portion 11b over that of the first portion 11a will decrease the pressure requirement for effective delivery of the material to be implanted.

The first and second portions 11a, 11b have approximately equal lengths, but this is governed by the anatomy of the site to be accessed. In the "average" percutaneous vertebroplasty situation, the first portion 11a is required to be about 1.5" long, as this is the length that is needed for traversing the cortical bone of the pedicle. Thus, the first portion should not be significantly enlarged due to the size constraints of the pedicle, the safety risks to the spinal column and aorta which are increased when the cannula size is increased intravertebrally, and by the desire to remove as little bone as possible when entering with the stylet and cannula, among other factors.

However, the portion of the cannula which will occupy the soft tissues can be significantly expanded without substantially adversely effecting the patient. Given the benefits of reducing the required injection pressure and ensuring a better delivery of the bone implant material, such a modification becomes a viable option.

Figure 17:
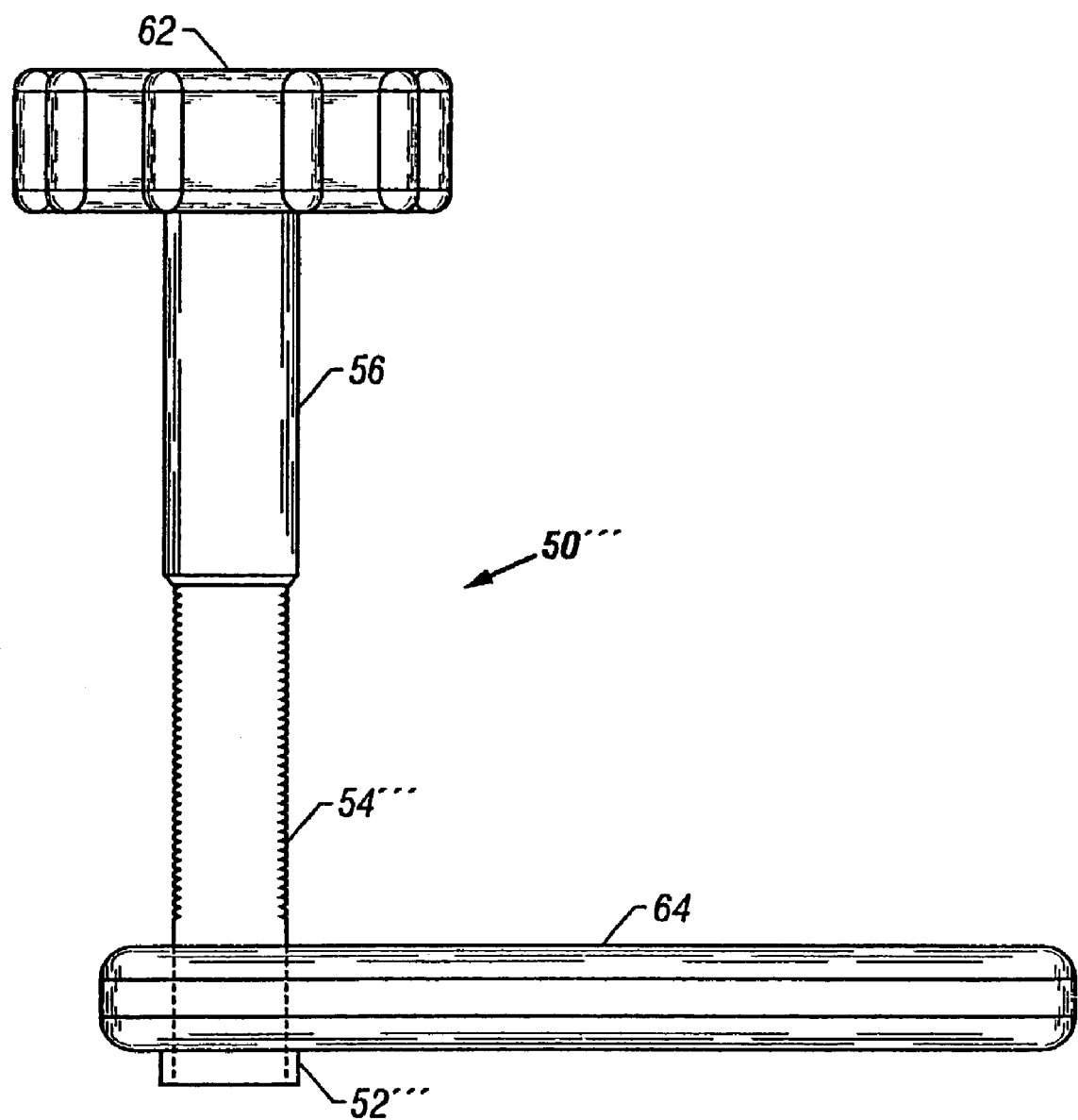
FIG. 17 shows the high pressure applicator used in FIG. 16.

The pressure applicator 50''' is essentially the same as that in the embodiment 50, with modifications as follows. The pressure applicator 50''' is provided with a fitting 52''' (FIG. 17) which is designed to form a pressure tight connection with the connector 18' and is therefore of a significantly larger diameter than the connector 52. Additionally, the first column 54' is essentially open at both ends 54a''' and 54b''' as it does not taper or tapers much less than the previous embodiment at opening 54b'''. As mentioned above, the preferred type of connection is a Luer-lock type connection, but alternative, equivalent types of connectors may be employed.

Like pressure applicator 50, the components of the pressure applicator 50''' are all preferably formed of amorphous nylon. The housing or second column or any portions which do not contact the implant material, may be formed of ABS plastic. Additionally, any other materials which are durable, sterilizable, biofriendly and nonreactive with the particular implant materials to be contained therein, e.g., stainless steel, polypropylene, could be readily substituted.

Figure 16:
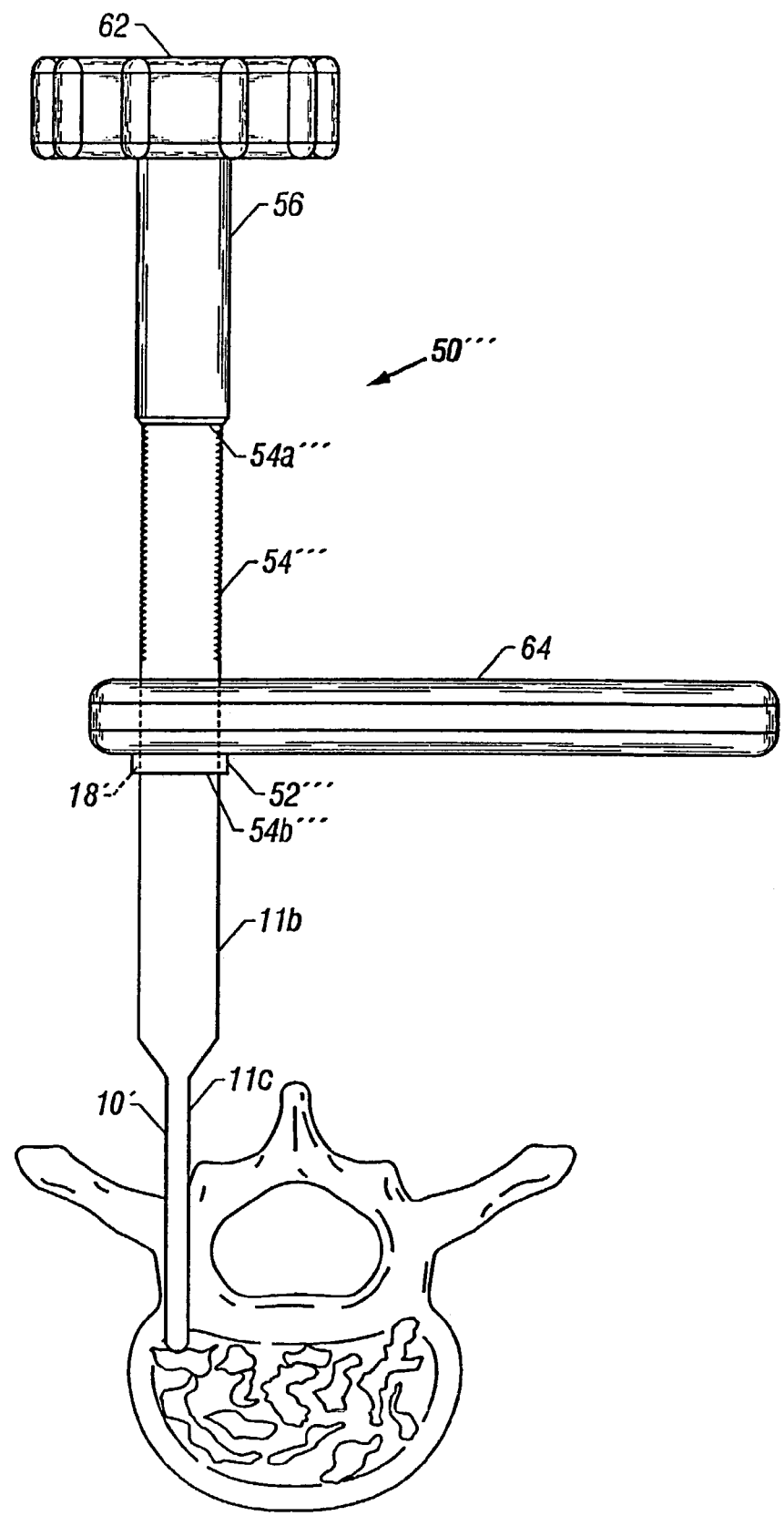
FIG. 16 shows an alternative embodiment of the high pressure applicator in FIG. 6.

Although the above modifications with regard to FIG. 16 have been described and shown as applied to the applicator 50, it is noted that similar modifications can be effected with regard to applicators 50', 50'', 70, and 70'. It is further recognized that even embodiments 90 and 90' could be so modified, although this would also likely require modification of the disposable syringes which might not then be as readily accessible commercially.

Prior to mounting the pressure applicator 50' on the cannula 10', a hard tissue implant material 66 is loaded into the first column 54 and the second column 56 is connected with the first column 54 in preparation for implantation. The pressure applicator 50' is then mounted onto the cannula 10' as shown in FIG. 16. The operator next grasps the handle 62 in one hand and the handle 64 in the other and begins to torque the handle 62. When operated as described, the pressure applicator is capable of generating controllable and sustainable pressures of up to about 3000 psi within the columns, which is a high driving force that is applied to the implantable material 66.

Alternative to the direct connection of the pressure applicator 50 to the connector 18 via fitting 52, as shown in FIG. 6, a high pressure tubing 70 may be and preferably is interconnected between the pressure applicator 50 and the cannula 10, as shown in FIG. 18. In addition to a high pressure rating, it is preferable that the tubing be a substantially non-compliant tubing, to obviate problems of "oozing" and overfilling that occur when there is too much compliance in a high pressure implantation system. Preferred examples of high pressure, substantially non-compliant tubings include PEEK tubing, and other polymers such as Nylon, PTFE, and FEP which may be radially reinforced with a no-stretch coil such as a flat wire spring of stainless steel, aramid fibers such as Kevlar, etc. A more detailed description of high pressure, substantially non-compliant tubings which are suitable for tubing 70 is given in copending application Ser. No. 09/276,062, filed Mar. 25, 1999 and entitled "Non-Compliant System for Delivery of Implant Material". application Ser. No. 09/276,062 is hereby incorporated herein its entirety by reference thereto.

Similar to previous modifications, this modification applies to all other embodiments, in addition to the applicator 50 which is specifically referred to. The tubing 70 has mate 72 and female 74 connectors for forming pressure tight seals with, fitting 52 and connector 18, respectively. The tubing 70 enables both the applicator 50, and thus the user's hands to be distanced from the radiographic field or other viewing field, which is advantageous both for safety purposes as well as improving the procedure. This embodiment is particularly advantageous for the most frequent set-ups where bi-planar viewing is performed and two imaging devices are oriented at 90° to one another about the implantation site. One of the advantages which is gained that improves the procedure, is that the viewing instrumentation can be moved closer to the actual implantation site, thereby providing a more magnified view.

It is preferred that the tubing 70 is mounted to the pressure applicator prior to mounting on the cannula fitting 13. After filling the pressure applicator with implant material as described above, the tubing 70 is mounted to fitting 52. A small amount of pressure is next applied to the implant material to express the implant material until a minimal amount exits the open end of the tubing (i.e., the end where connector 74 is located). The tubing 70 is then connected to the connector 18 of the cannula 10 for implantation of the implant material into the desired location. Although the foregoing is the desired order of connection so that the air space in the tubing can be prefilled with implant material, it is not the only possible progression for the procedure. Alternatively, the tubing 70 can be connected to the fitting 13 of the cannula 10 and the tubing 70 and cannula 10 are then backfilled with saline, implant material, or other biocompatible fluid to displace any air residing in the structures. After filling of the pressure applicator 50 with implant material, the tubing can be connected to the fitting 52 and implantation of the implant material can be rapidly commenced thereafter.

Figure 20:
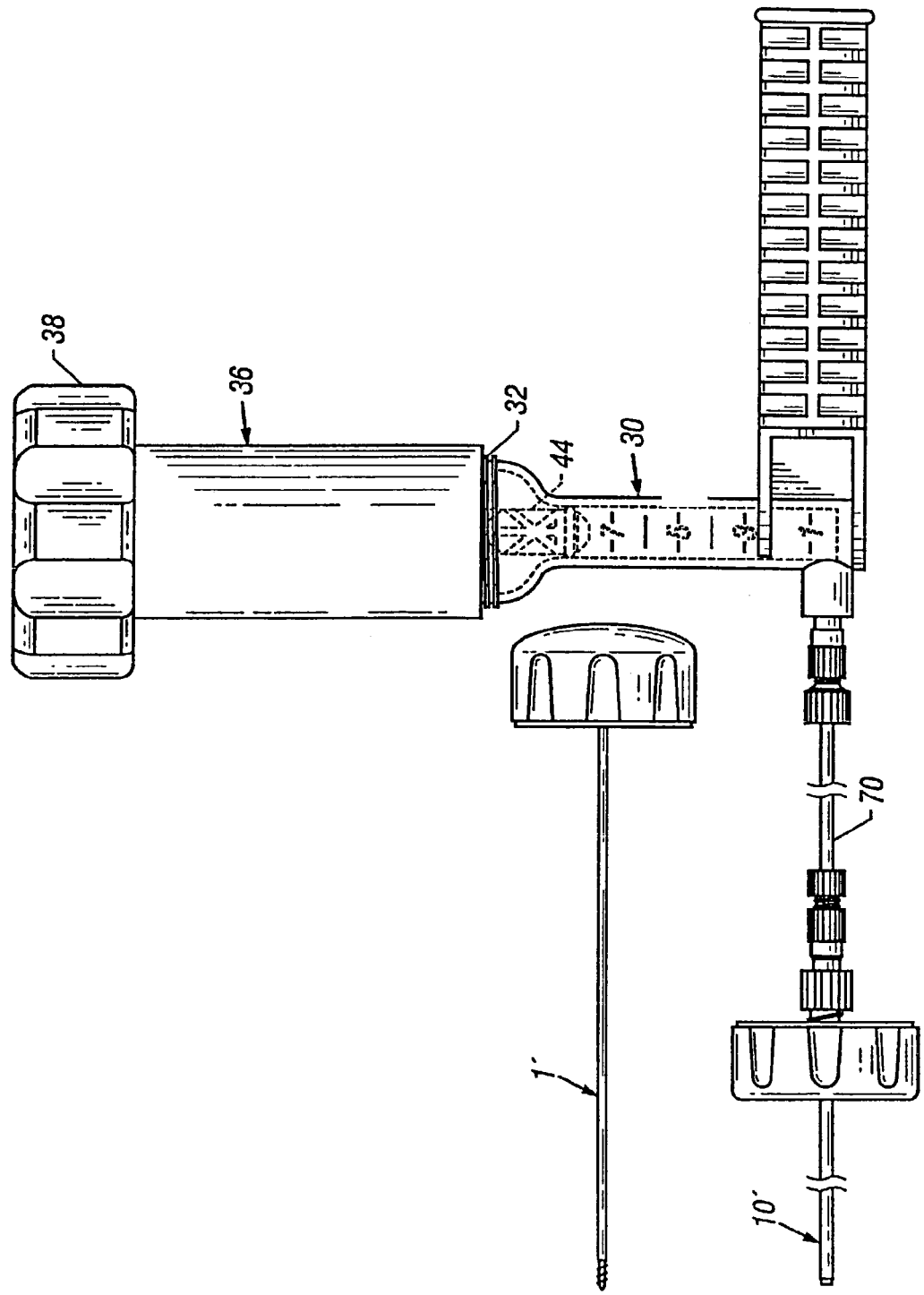
FIG. 20 shows a high pressure applicator having an enlarged introduction section, a substantially noncompliant tubing, a cannula and a stylet for use in performing a percutaneous implantation.

FIG. 20 shows a high pressure applicator having an enlarged introduction section, a substantially noncompliant tubing, a cannula and a stylet for use in performing a percutaneous implantation. High pressure applicator having the feature of an enlarged introduction section are further disclosed and claimed in a co-owned application filed concurrently herewith, entitled "High Pressure Delivery System". The application Ser. No. 11/369,662 filed concurrently herewith entitled "High Pressure Delivery System" is hereby incorporated by reference thereto in its entirety.

Figure 21:
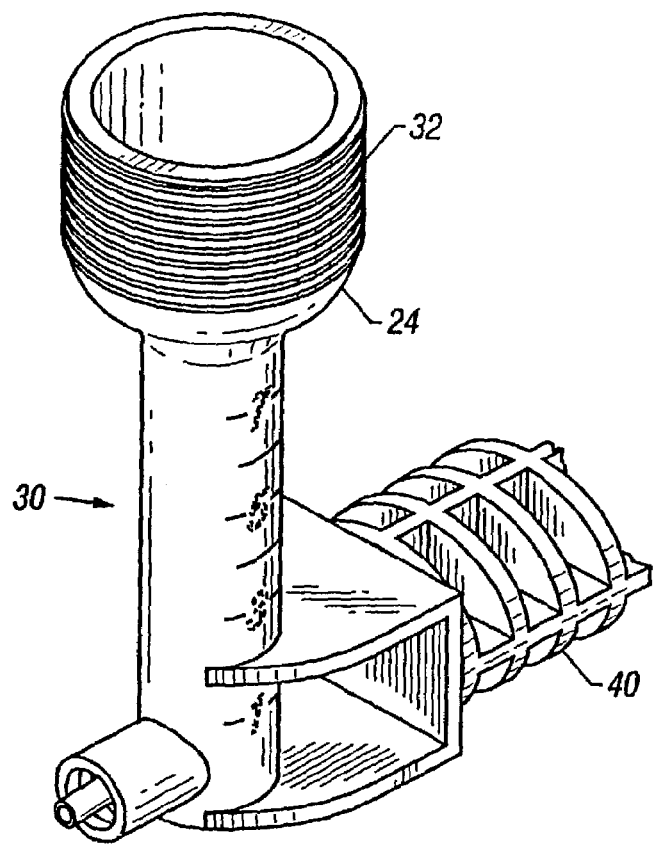
FIG. 21 shows the first column and a portion of the handle of the high pressure applicator in FIG. 20.

FIG. 21 is an enlarged detail showing of the first column 30 and a portion of the handle 40 of the high pressure applicator shown in FIG. 20. The open end portion of the first column 30 is formed as an introduction section 24 which has a slightly larger cross-sectional area than that of the portion of the first column 30 adjacent to it. Providing a larger size or diameter introduction section 24 enables the introduction of the plunger 44 into the implant material without simultaneously forming a seal where compliant bubbles may be trapped. Put another way, the differential in sizes is provided so that when the smaller diameter portion of the first column 30 is fully filled and the introduction section 24 is at least partially filled, the end of the plunger 44 which might otherwise trap air bubbles resulting in system compliance will be dipped in the implant material thereby allowing for the exclusion of air bubbles prior to driving it into the smaller diameter portion.

The introduction section 24 may be relatively close in size to the adjoining smaller diameter portion to provide only a surrounding dam for a meniscus poured over the smaller diameter portion. Since the amount of material that needs to be provided in the introduction section need not be great to facilitate the venting or purging as described above, it is better to only introduce slightly more implant material than will fill the smaller diameter portion. Introduction of a larger amount of implant material is not only wasteful, but may result in material drainage out of the introduction section into other parts of the applicator—especially when the applicator is inverted or turned as will often be the case in preparing PMMA implant material for delivery.

To help account for the possibility of excess implant material and associated potential of fouling of the applicator with such an excess, a larger size of the introduction section 24 than strictly required for the venting feature discussed above may be used to act as a catch basin for excess material. This will provide a larger margin of error in pouring implant material into the applicator before overflowing the introduction section 24 will occur. Further, the walls of such an enlarged catch basin may help to prevent contamination of the applicator by virtue of adherence of the implant material to the surface area provided during inversion or agitation of the applicator.

In the example shown in FIGS. 20 and 21, the introduction section is provided with threads 32 which engage with threads (not shown) on the interior of the second column 36, similar to the arrangements provided in the embodiments shown in FIGS. 6-9. Handle 38 is provided for torquing the second column 36 with respect to the first column 30. Accordingly, the concept of the introduction section could be applied to any of those embodiments, and could also be adapted to the embodiments having threading internally of an introduction section with external threading on a second column. The concept is also generally applicable to the embodiments shown in FIGS. 13 and 14, where an introduction section could be provided in the barrel 152 of the syringe.

Figure 22:
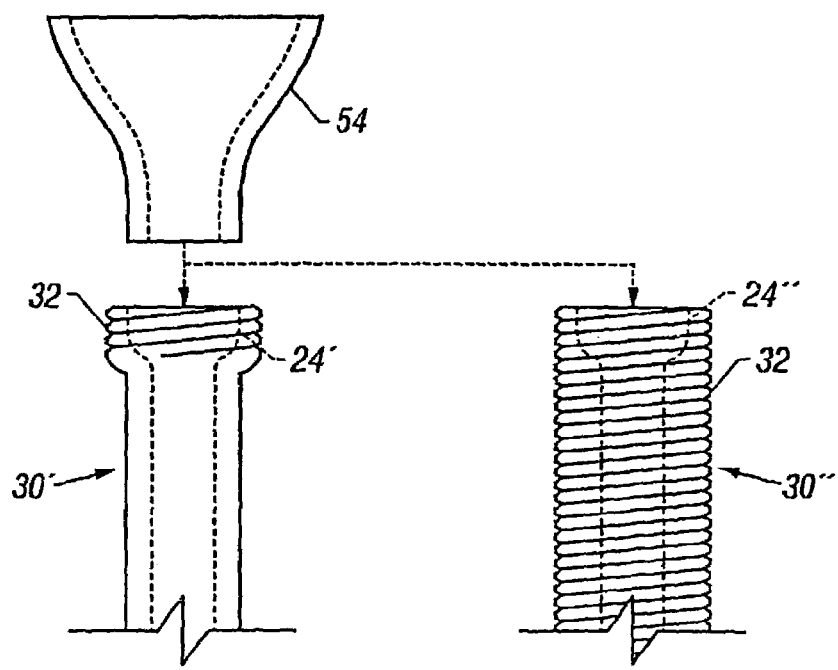
FIG. 22 shows alternate configurations of an end of the first column and an independent funnel useable with each.

FIG. 22 shows alternate configurations of an end of the first column 30' and 30", and an independent funnel 54 useable with each. The funnel or increased-size target region 54 may also be integrated into the introduction section 24 to aid in pouring implant material into the applicator. Drive threads may be placed on the exterior funnel 54. A presently preferred thread size is 1½-12 ACME 2.G 10° external. However, when no integral funnel is provided, a smaller introduction section 24', 24" may be used to provide a greater mechanical advantage. Additionally on the smaller introduction section, or alternatively on the larger introduction section, the drive threads placed exterior thereto may be of a finer pitch or higher thread count than those previously described to provide for greater mechanical advantage for generating higher driving pressures more easily. To help in loading material into the applicator when no integral funnel is used, a separate funnel element 54 may be provided to interface with the introduction section 24.

In the embodiments shown, the first column is advantageously about 0.50 inches in diameter and of a length of about 4 inches in order to provide sufficient volume for implant material for efficiency in performing vertebroplasty and yet have a small enough bore so that the mechanical advantage in applying pressure to the implant material is not overly affected as would be the case with a much larger bore. The preferred size range for the first column is between about 0.375 to about 0.75 inches with a length of between about 1.5 and 4.5 inches. The preferred capacitance of the first column is at least 5 cc, up to about 15 cc, as described above.

Further details as to the use or other aspects of the high-pressure implant system may be noted in the above referenced applications already referred to in describing the present invention which are herein incorporated by reference in their entirety. It is noted that this invention has been described and specific examples of the invention have been portrayed which may be advantageous. The use of those specific examples is, however, not intended to limit the invention in any way. Additionally, to the extent that there are variations of the invention which are within the spirit of the disclosure and yet are equivalent to the inventions found in the claims, it is the intent that the claims cover those variations as well. All equivalents are considered to be with in the scope of the claimed invention, even those which may have not been set forth herein merely for the sake of brevity. Also, the various aspects of the invention described herein may be modified and/or used in combination with such other aspects also described to be part of the invention or references discussed to form other advantageous variations considered to be part of the invention covered.

The invention claimed is:

1. A high pressure applicator for driving the delivery of a flowable tissue implant material to a target site, the high pressure applicator comprising:
   a body adapted to contain at least about 5 cc of the implant material, an elongate member comprising an enlarged end portion adapted to generate a high pressure within the body to drive the implant material from said body, wherein said body has a smooth inner wall portion and a radial access space, and wherein the body has an internally threaded member portion radially inset and axially spaced away from the smooth inner wall portion and adapted to threadingly interface with said elongate member for driving engagement therewith, thereby advancing said elongate member, and a removable section operable to be swung open or removed wherein removal or opening of the removable section opens the radial access space and exposes the smooth inner wall portion thereby allowing placement of the enlarged end section of the elongate member in the body from a radial direction and clear of the internally threaded member portion wherein the removable section detachably engages the body; and
   a substantially noncompliant tubing having a proximal end detachably connectable to said body, said tubing having a length such that both said applicator body and a user's hands may be distanced from a radiographic field covering the target site thereby reducing radiation exposure to the user.

2. The high pressure applicator of claim 1, wherein said removable section is hinged with respect to said body.

3. The high pressure applicator of claim 1, wherein said body comprises a syringe.

4. The high pressure applicator of claim 1, wherein said elongate member comprises threadings.

5. The high pressure applicator of claim 1, wherein said body further comprises a handle extending therefrom.

6. The high pressure applicator of claim 1, wherein said threaded member comprises a handle portion.

7. The high pressure applicator of claim 1, wherein said elongate member comprises a handle.

8. The high pressure applicator of claim 1, wherein second end of said elongate member comprises a sealing element.

9. The high pressure applicator of claim 8, wherein said sealing element is an O-ring.

10. The high pressure applicator of claim 1 further comprising a rigid cannula wherein said tubing comprises a distal end that is adapted to detachably connect with said rigid cannula.

11. A high pressure applicator kit for driving the delivery of a flowable tissue implant material to a vertebral body, the high pressure applicator kit comprising:

an applicator comprising a body adapted to contain at least about 5 cc of the implant material, an elongate member comprising an enlarged end portion adapted to generate a high pressure to drive the implant material from said body, wherein said body has a smooth inner wall portion and a radial access space, and wherein the body has an internally threaded member portion radially inset and axially spaced away from the smooth inner wall portion and adapted to threadingly interface with said elongate member for driving engagement therewith, thereby advancing said elongate member, and a removable section operable to be swung open or removed wherein removal or opening of the removable section opens the radial access space and exposes the smooth inner wall portion thereby allowing placement of the enlarged end section of the elongate member in the body from a radial direction and clear of the internally threaded member portion wherein the removable section detachably engages the body;

a substantially noncompliant tubing having a proximal end detachably connectable to said body, a rigid cannula, said cannula having a proximal end detachably connectable to a distal end of said tubing;

a stylet receivable within said cannula, said cannula and stylet terminating in a bone-penetrating distal end; and said tubing having a length such that said body is distanced from a radiographic field covering the target site.

12. The kit of claim 11 wherein said tubing is made of a polymer.

13. The kit of claim 12 wherein said tubing is made of PEEK.

14. The high pressure applicator of claim 1, wherein tubing is made of a polymer.

15. The high pressure applicator of claim 1, wherein tubing is made of PEEK.

16. The high pressure applicator of claim 1 wherein the elongate member is adapted to generate a high pressure of at least 1000 psi within the body.

17. The high pressure applicator of claim 1 wherein the elongate member is adapted to generate a high pressure of at least 1500 psi within the body.

18. The high pressure applicator of claim 1 wherein the elongate member is adapted to generate a high pressure of about 1000 psi to 3000 psi within the body.

* * * * *